(12) United States Patent
Olsen

(10) Patent No.: US 9,750,602 B2
(45) Date of Patent: Sep. 5, 2017

(54) METHODS OF PREDICTING THE POST-OPERATIVE POSITION OF AN IOL AND USES OF SUCH METHODS

(75) Inventor: Thomas Olsen, Aarhus (DK)

(73) Assignee: IOL INNOVATIONS, APS, Aarhus N (DK)

(*) Notice: Subject to any disclaimer, the term of this patent is extended or adjusted under 35 U.S.C. 154(b) by 485 days.

(21) Appl. No.: 14/003,151

(22) PCT Filed: Mar. 8, 2012

(86) PCT No.: PCT/EP2012/054010
§ 371 (c)(1),
(2), (4) Date: Sep. 4, 2013

(87) PCT Pub. No.: WO2012/120080
PCT Pub. Date: Sep. 13, 2012

(65) Prior Publication Data
US 2013/0345807 A1 Dec. 26, 2013

(30) Foreign Application Priority Data
Mar. 9, 2011 (GB) .................................. 1103970.8

(51) Int. Cl.
*A61F 2/16* (2006.01)
*A61B 3/00* (2006.01)
(Continued)

(52) U.S. Cl.
CPC .............. *A61F 2/16* (2013.01); *A61B 3/0025* (2013.01); *A61B 5/1072* (2013.01);
(Continued)

(58) Field of Classification Search
USPC ....................................................... 623/6.11
See application file for complete search history.

(56) References Cited

U.S. PATENT DOCUMENTS

| 5,282,852 A | 2/1994 | Capetan et al. |
| 2007/0083261 A1 | 4/2007 | Colvard et al. |

(Continued)

FOREIGN PATENT DOCUMENTS

| WO | 2006/053216 | 5/2006 |
| WO | 2006/053216 A2 | 5/2006 |

(Continued)

OTHER PUBLICATIONS

Binkhorst, R.D. "The optical design of intraocular lens implants." Ophthalmic Surg. 1975 Fall;6(3):17-31.
(Continued)

*Primary Examiner* — Thomas J Sweet
*Assistant Examiner* — Tiffany Shipmon
(74) *Attorney, Agent, or Firm* — Robert C. Netter, Jr.; Dann, Dorfmann, Herrell & Skillman

(57) ABSTRACT

The invention relates to the field of ophthalmic systems and procedures. In particular, the invention relates to the determination of the post-operative position of an intraocular lens (termed "IOL") in an eye of a patient undergoing lens replacement surgery, which involves determining the position of the existing crystalline lens in the pre-operative eye of the patient and using that information and a single numerical constant to predict the post-operative intraocular lens position. Related methods, and computer programs for performing the methods of the invention, are also disclosed.

10 Claims, 10 Drawing Sheets

Figure 1:
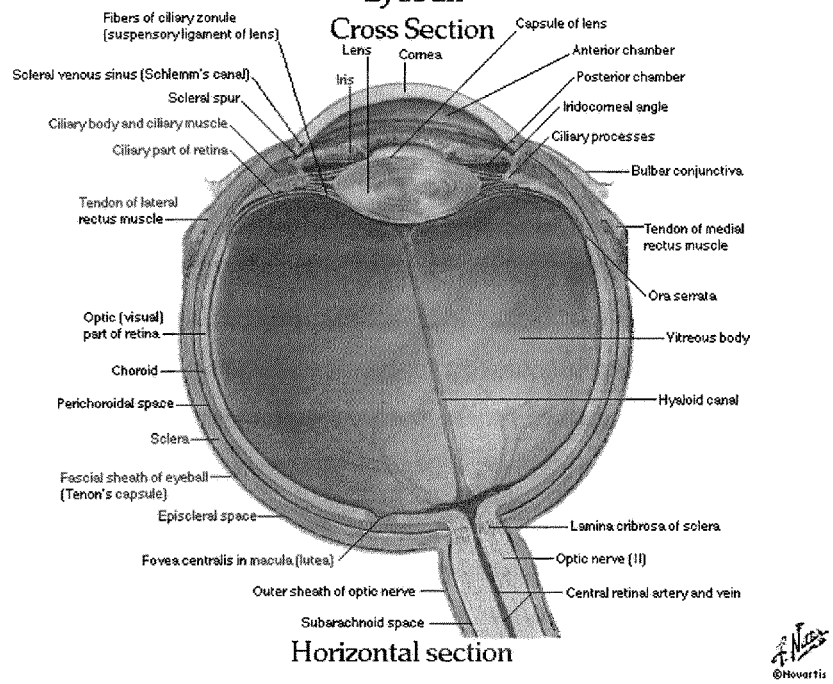

(51) Int. Cl.
  *A61B 5/107* (2006.01)
  *A61B 8/08* (2006.01)
  *A61B 8/10* (2006.01)
  *A61B 34/10* (2016.01)

(52) U.S. Cl.
  CPC .............. *A61B 8/0858* (2013.01); *A61B 8/10* (2013.01); *A61B 34/10* (2016.02); *A61F 2240/002* (2013.01)

(56) References Cited

U.S. PATENT DOCUMENTS

2009/0251664 A1 10/2009 Norby et al.
2010/0030225 A1 2/2010 Ianchulev

FOREIGN PATENT DOCUMENTS

| WO | 2010/028654 | | 3/2010 |
| WO | 2011/008609 | | 1/2011 |
| WO | 2011/008606 | A1 | 2/2011 |
| WO | 2011/008609 | A1 | 2/2011 |

OTHER PUBLICATIONS

Binkhorst, R.D. "Intraocular lens power." Int Ophthalmol Clin. 1979 Fall;19(3):83-94.
Colenbrander. "Calculation of the power of an iris clip lens for distant vision." Br J Ophthalmol. Oct. 1973;57(10):735-40.
Connors, R., et al. "Accuracy and reproducibility of biometry using partial coherence interferometry." J Cataract Surg. Feb. 2002;28(2):235-8.
Drexler, W., et al. "Partial coherence interferometry: a novel approach to biometry in cataract surgery." Am J Ophthalmol. Oct. 1998;126(4):524-34.
Dubbelman, M., et al. "Radius and asphericity of the posterior corneal surface determined by corrected Scheimpflug photography." Acta Ophthalmol Scand. Aug. 2002;80(4):379-83.
Dubbelman, M., et al. "The shape of the anterior and posterior surface of the aging human cornea." Vision Res. Mar. 2006;46(6-7):993-1001.
Dunne, M.C., et al. "Normal variations of the posterior corneal surface." Acta Ophthalmol (Copenh). Apr. 1992;70(2):255-61.
Findl, O., et al. "Influence of operator experience on the performance of ultrasound biometry compared to optical biometry before cataract surgery." J Cataract Refract Surg. Oct. 2003;29(10):1950-5.
Fyudorov S.N., et al al. "Calculation of the optical power of intraocular lenses." Invest Ophthalmol. Aug. 1975;14(8):625-8.
Gernet, H., et al. "[Intraocular lens planning. Geometric-optical and Sanders-Retzlaff-Kraff I and II formulas]." Ophtalmologie. Jan.-Feb. 1990;4(1):96-101. [Abstract].
Haigis, W., et al. "Comparison of immersion ultrasound biometry and partial coherence interferometry for intraocular lens calculation according to Haigis." Graefes Arch Clin Exp Ophthalmol. Sep. 2000;238(9):765-73.
Haigis, W., et al. "Pseudophakic correction factors for optical biometry." Graefes Arch Clin Exp Ophthalmol. Aug. 2001;239(8):589-98.
Hoffer, K.J. "The Hoffer Q formula: a comparison of theoretic and regression formulas." J Cataract Refract Surg. Nov. 1993;19(6):700-12.
Hoffer, K.J. "Clinical results using the Holladay 2 intraocular lens power formula." J Cataract Refract Surg. Aug. 2000;26(8):1233-7.
Holladay, J.T., et al. "A three-part system for refining intraocular lens power calculations." J Cataract Refract Surg. Jan. 1988;14(1):17-24.
Jansson F. and Kock E., "Determination of the velocity of ultrasound in the human lens and vitreous." Acta Ophthalmol (Copenh). 1962;40:420-33.

Kiss, B., et al. "Refractive outcome of cataract surgery using partial coherence interferometry and ultrasound biometry: clinical feasibility study of a commercial prototype II." J Cataract Refract Surg. Feb. 2002;28(2):230-4.
Olsen, T. and Funding, M. "Ray-tracing analysis of intraocular lens power in situ." J Cataract Refract Surg. Apr. 2012;38(4):641-7.
Olsen, T. and Gimbel, H. "Phacoemulsification, capsulorhexis, and intraocular lens power prediction accuracy." J Cataract Refract Surg. Nov. 1993;19(6):695-9.
Olsen, T. and Thorwest, M. "Calibration of axial length measurements with the Zeiss IOLMaster." J Cataract Refract Surg. Jul. 2005;31(7):1345-50.
Olsen, T., et al. "Theoretical versus SRK I and SRK II calculation of intraocular lens power." J Cataract Refract Surg. Mar. 1990;16(2):217-25.
Olsen, T. "On the Stiles-Crawford effect and ocular imagery." Acta Ophthalmol (Copenh). Feb. 1993;71(1):85-8.
Olsen, T., et al. "Calculation of intraocular lens power: a review." Acta Ophthalmol Scand. Aug. 2007;85(5):472-85. Epub Apr. 2, 2007.
Olsen, T., et al. "Prediction of postoperative intraocular lens chamber depth." J Cataract Refract Surg. Sep. 1990;16(5):587-90.
Olsen, T., et al. "Accuracy of the newer generation intraocular lens power calculation formulas in long and short eyes." J Cataract Refract Surg. Mar. 1991;17(2):187-93.
Olsen, T., et al. "Prediction of pseudophakic anterior chamber depth with the newer IOL calculation formulas." J Cataract Refract Surg. May 1992;18(3):280-5.
Olsen, T., et al. "Intraocular lens power calculation with an improved anterior chamber depth prediction algorithm." J Cataract Refract Surg. May 1995;21(3):313-9.
Olsen, T. "Theoretical vs empirical prediction of aphakic refraction." Arch Ophthalmol. Aug. 1987;105(8):1042-5.
Olsen, T. "On the calculation of power from curvature of the cornea." Br J Ophthalmol. Feb. 1986;70(2):152-4.
Olsen, T. "Prediction of intraocular lens position after cataract extraction." J Cataract Refract Surg. Jul. 1986;12(4):376-9.
Olsen, T. "Theoretical approach to intraocular lens calculation using Gaussian optics." J Cataract Refract Surg. Mar. 1987;13(2):141-5.
Olsen, T. "Theoretical, computer-assisted prediction versus SRK prediction of postoperative refraction after intraocular lens implantation." J Cataract Refract Surg. Mar. 1987;13(2):146-50.
Olsen, T. "Prediction of the effective postoperative (intraocular lens) anterior chamber depth." J Cataract Refract Surg. Mar. 2006;32(3):419-24.
Packer, M., et al. "Immersion A-scan compared with partial coherence interferometry: outcomes analysis." J Cataract Refract Surg. Feb. 2002;28(2):239-42.
Preussner, P-R., et al. "Ray tracing for intraocular lens calculation." J Cataract Refract Surg. Aug. 2002;28(8):1412-9.
Preussner, P-R., et al. "Intraocular lens calculation accuracy limits in normal eyes." J Cataract Refract Surg. May 2008;34(5):802-8. doi: 10.1016/j.jcrs.2008.01.015.
Retzlaff, J.A., et al. "Development of the SRK/T intraocular lens implant power calculation formula." J Cataract Refract Surg. May 1990;16(3):333-40.
Retzlaff, J. "A new intraocular lens calculation formula." J Am Intraocul Implant Soc. Apr. 1980;6(2):148-52.
Sanders, D.R., et al. "Comparison of the SRK II formula and other second generation formulas." J Cataract Refract Surg. Mar. 1988;14(2):136-41.
Sanders, D.R., et al. "Comparison of the SRK/T formula and other theoretical and regression formulas." J Cataract Refract Surg. May 1990;16(3):341-6.
Sanders, D.R., et al. "Comparison of the accuracy of the Binkhorst, Colenbrander, and SRK implant power prediction formulas." J Am Intraocul Implant Soc. 1981 Fall;7(4):337-40.
Vogel, A., et al. "Reproducibility of optical biometry using partial coherence interferometry : intraobserver and interobserver reliability." J Cataract Refract Surg. Dec. 2001;27(12):1961-8.
Stiles, W.S. and B. H. Crawford. "The Luminous Efficiency of Rays Entering the Eye Pupil at Different Points." Proc. R. Soc. Lond. B 1933; (112): 428-450.

(56) References Cited

OTHER PUBLICATIONS

Olsen, T. and Corydon L. "We Don't Need Fudge Factors in IOL Power Calculations." Eur J Implant Refract Surg Mar. 1993; (5): 51-54.
Baker, T.Y. "Ray tracing through non-spherical surfaces." Proc. Phys. Soc. 1943; (55): 361-364.
Binkhorst, R.D. "Intraocular Lens Power Calculation." Int. Opthamalmol Clin. 1978; (19): 237-252.
Bennett & Rabbetts. Clinical Visual Optics, Butterworth, London. pp. 234-238. 1984.
Born & Wolf. Principles of Optics, 6th Edition. Pergamon Press, New York. pp. 233-235. 1980.
Gullstrand. Ed. Hemmholz. Handbuch der Physiologischen Optik. Hamburg and Leizig, Hamburg. pp. 1-105. 1909.
Norby, S., et al. "Clinical application of the lens haptic plane concept with transformed axial lengths." Journal of Cataract and Refractive Surgery. Jul. 1, 2005;31(7):1338-1344.
Olsen, T. "Intraocular lens power calculation with an improved anterior chamber depth prediction algorithm." Journal of Cataract and Refractive Surgery. Jan. 1, 1995;21(1): 313-319.
Gullstrand. Ed. Southall JPC. Optical Society of America, pp. 358-382. 1924. [English translation of Gullstrand. Ed. Hemmholz. Handbuch der Physiologischen Optik. Hamburg und Leizig, Hamburg. pp. 1-105. 1909.).
Haigis, W. The Haigis formula. In: Intraocular lens power calculations. (Ed.Shammas HJ). Slack Inc, 2004; 5-57.
Olsen, T. The Olsen formula. In: Intraocular lens calculations. (Ed.Shammas HJ). Thorofare, N.J.: Slack Inc, 2004; 27-40.
Wikipedia. Intraocular Lens entry. Retrieved Feb. 16, 2012. <http://en.wikipedia.org/wiki/Intraocular_lens>.
IoL Innovations. Non-confidential Memo. Feb. 2, 2012.

METHODS OF PREDICTING THE POST-OPERATIVE POSITION OF AN IOL AND USES OF SUCH METHODS

This application is a §371 application of PCT/EP2012/054010, filed Mar. 8, 2012, which in turn claims priority to GB Application 1103970.8, filed Mar. 9, 2011. The entire disclosure of each of the foregoing applications is incorporated by reference herein.

The invention relates to the field of ophthalmic systems and procedures. In particular, the invention relates to the determination of the post-operative position of an intraocular lens (termed "IOL") in an eye of a patient undergoing lens replacement surgery, which involves determining the position of the existing crystalline lens in the pre-operative eye of the patient and using that information and a single numerical constant to predict the post-operative intraocular lens position. Related methods, and computer programs for performing the methods of the invention, are also disclosed.

Lens replacement surgery involves removing the existing biological crystalline lens from the eye and implanting an artificial intraocular lens (IOL). Typically, the IOL is implanted into the empty lens capsule (sometimes referred to as "the-bag") which is left following removal of the biological lens material.

An IOL usually consists of a small plastic lens with plastic side struts (called haptics) to hold the lens in place within the capsular bag inside the eye. IOLs were traditionally made of an inflexible material (such as polymethylmethacrylate (PMMA), although this has largely been superseded by the use of flexible materials. Most IOLs fitted today are fixed monofocal lenses matched to distance vision, but other types are available, such as multifocal IOLs (which provide multiple-focused vision at far and near distances), adaptive IOLs (which provide limited visual accommodation) and toric IOLs (which provide correction for astigmatism).

Lens replacement surgery may be performed for a number of reasons.

Cataract (a clouding of the crystalline lens which obstructs the passage of light through the eye and obscures vision) is one of the leading causes of blindness, and surgery to remove the cataract and implant an intraocular lens is one of the most commonly-performed surgical procedures world-wide. However, in recent years the overall improvement in safety and efficacy of lens replacement surgery and the development of new IOL designs has broadened the indication for lens surgery to encompass not only patients with cataract, but also patients with refractive problems like myopia (near-sightedness), hypermetropia (short-sightedness) and presbyopia (spectacle-dependence in reading), and astigmatism (cylinder dependence of spectacle correction).

Figure 2:
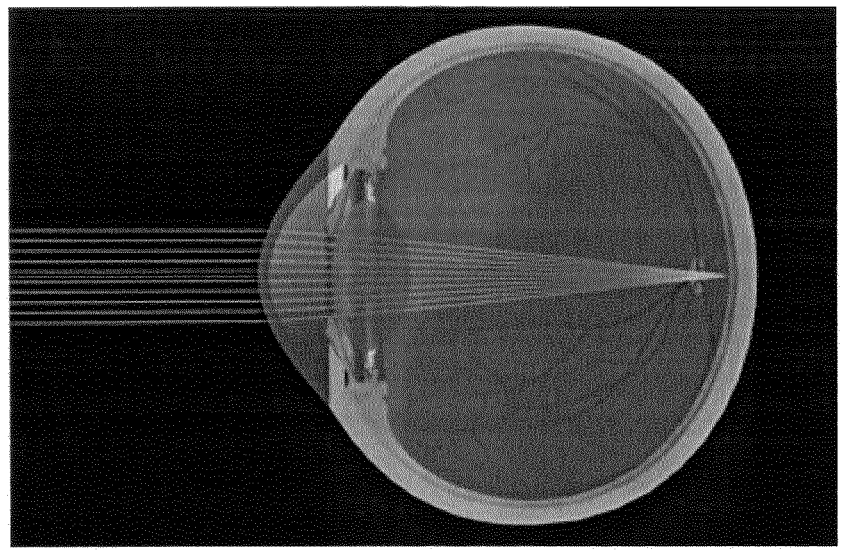

The eye is not a simple physical lens system but rather a biological organ in which various internal surfaces and interfaces (such as the anterior and posterior corneal surfaces and the anterior and posterior lens surface) contribute to the deflection of light and formation of an image on the retina where it is perceived (see FIGS. 1 and 2).

As the precise optical properties and dimensions of the eye vary from patient to patient, selection of an IOL with suitable optical properties (such as dioptric power both spherical and cylindrical, asphericity as well as higher order aberrations) is crucial if vision is to be clear in a given eye. If the optical properties of the IOL implant match the optical properties and dimensions of the eye, the patient has a good chance that vision after surgery will be good and that spectacles will not be required, irrespective of whether spectacles were needed before surgery.

Because the small artificial intraocular lens is implanted into the empty capsule of the larger biological lens and because the capsule contracts as a result of the healing process after surgery, the exact physical position the IOL will occupy within the eye is often not known until after implantation. Furthermore, because the position of the intraocular lens cannot actually be measured until after surgery, its likely position must be estimated before surgery.

Clearly, the physical position of the IOL can vastly affect the way that light is refracted within the eye—for example, an IOL positioned closer to the cornea will focus light more anteriorly than an IOL that is further from the cornea, and each result in different spectacle correction in front of the eye to bring focus to the retina. Likewise, the effect of higher order aberrations build into the IOL on the eye's total optical performance will also be affected by the anterio-posterior location of the IOL within the eye. Thus, an important consideration when selecting an IOL implant is the prediction of the physical position of the implanted IOL in that eye.

Many approaches and mathematical formulae have been described which seek to calculate the IOL power to be used in surgery. However, because all of the presently available formulae use simplified models for the optics of the eye they require a number of empirically derived corrective terms and personalisation factors to be calculated in retrospect from observed data in order to adjust the formula to real clinical life. Examples of such "fudge" factors include the "A-constant" (SRK-formula), "Surgical Factor" (Holladay) or "effective ELP or effective Anterior Chamber Depth ("ACD") (Hoffer or Binkhorst formula). Whilst those factors ensure that predictions with the particular formula are accurate in the average case, they do not always provide an accurate prediction in the individual case. One reason for the inaccuracy of current methods is the insufficiency to predict the IOL position in the individual case.

Accordingly, whilst the current approaches and formulae have been used with some success over the years, none yet provides a perfect tool for predicting the post-operative IOL position that works for each patient—accordingly, even where the current approaches and formulae are used, a patient may still end up with imperfect vision after surgery due to implantation of an IOL that does not have suitable optical properties for that eye.

The present invention addresses the problems in the prior art.

In a first aspect, the invention provides a method for predicting the post-operative position of a replacement intraocular lens in an eye of a patient, the method comprising the steps of:
  (i) determining the position of the existing crystalline lens in the pre-operative eye of the patient;
  (ii) determining the thickness of the crystalline lens in the pre-operative eye of the patient; and
  (iii) predicting the post-operative position of the intraocular lens relative to the position of the crystalline lens in the pre-operative eye of the patient, as a proportion of the thickness of the crystalline lens in the pre-operative eye of the patient,
    wherein the proportion is defined by a single numerical constant (C) which is determined by the intraocular lens type.

As discussed in more detail below and in the accompanying Examples, the present invention provides a more accurate method for predicting, before surgery, the post-operative position of a replacement IOL in an eye of a patient.

The invention is based on the inventor's discovery that an IOL will locate itself at a defined position within the post-operative eye when it has been inserted into the empty capsule. That position can be described as a ratio of the thickness of the crystalline lens in the pre-operative eye of the patient. Accordingly, the post-operative position of an IOL is related to certain defined anatomical and physical characteristics of the pre-operative eye—in particular, the position and the thickness of the crystalline lens in the pre-operative eye of the patient. Thus, in light of the inventor's discovery, the measurement of certain physical parameters in the eye of a patient prior to surgery (in particular, the crystalline lens position and thickness) can be used to predict the specific post-operative position that an implanted IOL will occupy in the eye of that patient.

As explained in the accompanying Examples, the inventor's discovery arose from detailed analyses of eye-operated individuals with an actual IOL implant before and after surgery, in which various physical parameters that may influence the position of the IOL were measured. Statistical analysis of that data revealed where those parameters were related and allowed a surprisingly simple formula to be developed to express the measured parameters as a function of one another. That analysis revealed that the post-operative position of the implanted IOL could be accurately predicted using that formula along with the physical parameters taken from the eye before surgery.

Once the post-operative position of the IOL has been predicted, an accurate calculation (and prediction) of the most appropriate optical properties of the IOL (such as lens refractive power and other optical properties) to be implanted during surgery can be made. Such calculations and predictions are made by modelling the eye and the refraction of light within it. Methods for providing a detailed and correct model of the eye and an IOL implant require the correct interpretation of the various measurable physical parameters of the eye and the optical and physical properties of the plurality of interfaces and surfaces in the eye. Such methods involve both so-called 'thick lens' paraxial ray tracing methods and exact ray tracing methods as described herein, and are also known in the art (as discussed, for example, in WO 2010/028654).

Thus, the present invention differs from previous systems and methods in that:

(1) In the present invention, the prediction of the IOL position after surgery is separated from the optical formula described in the prior art, and is instead based on a true, physically-defined post-operative position of the IOL (preferably using a post-operative anterior chamber depth measurement), rather than a virtual post-operative position (such as a virtual effective lens position or "ELP"); and (2) In the present invention, the prediction of the post-operative position of the IOL can be made from an accurate measurement of the position and thickness of the crystalline lens of the patient before surgery, and (3) In the present invention, the physical prediction of the position of the IOL can be used in a realistic optical ray tracing model to accurately reflect the optics of the eye based on the measured and the predicted data. In this way the most appropriate optical properties of the IOL to be implanted can be made.

It will be appreciated that the position of the crystalline lens in step (i) can be determined in a number of ways, based on one or more measurements taken from the pre-operative eye. Preferably, the axial position of the crystalline lens in the pre-operative eye of the patient is determined, which can be performed accurately using (for example) partial coherence interferometry, which is done with a laser (for example, using a Lenstar LS900 by the Haag-Streit company, Switzerland).

It will also be appreciated that the thickness of the crystalline lens in the pre-operative eye of the patient can be determined in a number of ways, based on one or more measurements taken from the pre-operative eye. For example, the lens thickness can be determined by measuring the relative position of its front and back surface within the eye, for example using ultrasound, laser interferometry or laser biometry.

By "pre-operative eye of a patient" we include an eye before removal of its natural, biological crystalline lens. Those in the art frequently refer to such an eye as a "phakic" eye.

By "post-operative eye of a patient" we include an eye after removal of the natural, biological crystalline lens and after implantation of an IOL. Those in the art frequently refer to such an eye as a "pseudophakic" eye.

By "crystalline lens" we include the natural biological crystalline lens found in the eye.

As is well known, the crystalline lens is not uniform in thickness but has an ellipsoid or biconvex shape. By "thickness of the crystalline lens" we include the axial distance (along the line of sight) from the anterior surface to the posterior surface of the crystalline lens when it is in a relaxed state. The relaxed state is the non-accommodating state when the eye is distance-focused—however, that state becomes less important with the age of the patient because the ability to accommodate is gradually lost during life; for example, in humans from the age of 45 years old and onwards, it becomes very small and cannot influence the thickness of the lens.

By "intraocular lens" or "IOL" we include an artificial lens for implantation into the capsular bag in the eye. IOLs typically comprise a plastic lens with plastic side struts (called haptics) to hold the lens in place within the capsular bag. IOLs may be made of inflexible materials (such as PMMA) or flexible materials (such as silicone or acrylic). IOLs vary in terms of their optical properties (such as their spherical and cylindrical dioptric power, asphericity, and other higher orders of aberrations), and the IOL may be a fixed monofocal lens (matched to distance vision), a multi-focal lens (which provides multiple-focused vision at far and near distances); or an adaptive lens (which provides limited visual accommodation).

A key aspect of the present invention is the single numerical constant, termed "C".

The present invention is widely applicable and can be used with a range of different patient types—including humans (of all races and nationalities) and other mammals (such as a mammal of agricultural or commercial value, including horse, cow, pig, sheep, dog, cat, and rabbit). It will be appreciated that the dimensions and optical characteristics of an eye will vary between different animal types, between species and, in humans, between nationalities and races. Accordingly, the numerical constant (C) is determined not only by the IOL type but also by the patient type and the approach used to implant the IOL in the eye.

Preferably, the numerical constant (C) defines the relationship between the post-operative position of the intraocular lens in the eye of one or more eye-operated individuals, relative to the position and thickness of the crystalline lens in the pre-operative eye of the one or more eye-operated individuals.

More preferably, that numerical constant (C) is calculated using data obtained from two or more eye-operated individuals to whom that IOL type has been implanted into the eye using the same implantation approach.

It will be appreciated that the numerical constant (C) should be calculated using data from eye-operated individuals that are appropriate based on the particular patient type that is undergoing lens replacement surgery. As discussed above, the dimensions and optical characteristics of an eye will vary between different animal types, between species and, in humans, between races. For example, in humans, the eyes of Asian races have a different proportion between the anterior and the posterior segment of the eye compared to Caucasians—that is, an Asian eye will have a relatively shorter anterior segment and longer posterior segment as compared to a Caucasian eye.

In light of those differences, data obtained from appropriate eye-operated individuals should be used when calculating the numerical constant (C). For example, where the patient is a dog, the eye-operated individuals used to calculate the numerical constant (C) should also be dogs (and preferably, the same species of dog). Where the patient is a human, the eye-operated individuals used to calculate the numerical constant (C) should preferably be of the same race. Those skilled in the art will be aware of the relevant differences in eye dimension and optical characteristics and will be able to select appropriate eye-operated individuals for calculation of the numerical constant (C).

As demonstrated in the accompanying examples, data need only be obtained from very few eye-operated patients in order to accurately calculate the numerical constant, C. Preferably, the number of eye-operated individuals from whom data is obtained is: 2 or 3 or 4 or 5 or 6 or 7 or 8 or 9 or 10 or 20 or 30 or 40 or 50 or 60 or 70 or 80 or 90 or 100 pr 200 or more eye-operated individuals.

Conveniently, the numerical constant (C) defines a fraction of the thickness of the crystalline lens in the pre-operative eye of the two or more eye-operated individuals.

In one embodiment, the invention provides a method in which the IOL type is adapted for implantation into the capsular bag in the eye. Such IOLs are well known to those in the art.

Companies manufacturing IOLs are well known and include Alcon Laboratories: (which manufactures acrylic one-piece foldable IOLs termed Acrysof and Restor, among others); Rayner Intraocular Lenses (which manufactures a range of foldable implants termed Superflex and T-flex among others); Abbott Medical Optics (which manufactures acrylic one-piece foldable IOLs such as Tecnis® Aspheric IOL, Tecnis® Multifocal IOL, ReZoom® Multifocal IOL); Carl Zeiss Meditec (which manufactures a range of monofocal, multifocal and toric IOLs belonging to the Acri.Lisa series); Bausch & Lomb; Corneal; Hoya; Topcon.

Preferably, the IOL is implanted into the capsular bag in the eye. As is well known, the standard approach for performing such surgery is to open the anterior part of the crystalline lens capsule by a technique called 'capsulorhexis' which ensures a circular opening through which the lens matter is removed and through which the IOL is inserted. The capsule can be opened by different techniques (by tearing, by cutting, by burning, by laser) but the preferred placement of the IOL is always in-the-bag. The lens matter is often removed using 'phaco-emulsification' which uses ultrasound to disintegrate and aspirate the lens matter through a small incision; alternatively, the lens matter may be disintegrated manually or using a femto-second laser. Once the lens matter has been removed, the IOL is implanted through the opening in the anterior capsule and placed in the empty bag. This is the currently accepted method for performing lens surgery throughout the world.

It will be appreciated that the position of the IOL within the post-operative eye (and hence the numerical constant, C) may be influenced by the geometry of the IOL that is implanted, particularly because the diameter, shape and mechanical properties of the haptics may influence how the IOL will be pushed forward or backward as a result of the gradual contraction of the capsule after surgery. However, as demonstrated in the accompanying Examples, the variation in the C value obtained using two different IOL types is surprisingly small. Accordingly, the method of the present invention may be performed using any IOL which is adapted for implantation into the capsular bag in the eye, and which is implanted into the capsular bag in the eye.

The methods of the present invention are not used with implantation methods or IOL types that do not involve in-the-bag implantation. Such implantation methods and IOL types may be used when the lens capsule is not intact or is missing.

As discussed in the accompanying Examples, in a preferred embodiment the numerical constant (C) is calculated from data obtained from two or more eye-operated individuals using the following formula:

$$C = (IOL_{measured} - ACD_{pre})/LT$$

wherein:

$IOL_{measured}$ is the measured position of the intraocular lens in the eye of the eye-operated individual after surgery, which may be defined, for example, by the anterior chamber depth of the eye of the eye-operated individual. In a preferred embodiment, $IOL_{measured}$ is the measured position to the centre of the intraocular lens, which may be calculated by adding together the measured anterior chamber depth in the eye of an eye-operated individual after surgery and half of the IOL thickness.

$ACD_{pre}$ is the position of the anterior surface of the crystalline lens from the corneal surface in the eye of the eye-operated individuals before surgery; that position can be determined, for example, by measuring the Anterior Chamber Depth of the eye of the eye-operated individual before surgery;

LT is the thickness of the crystalline lens in the eye of the eye-operated individual before surgery.

Thus, the numerical constant (C) can be calculated by a method comprising the steps of: measuring the position and thickness of the crystalline lens in the eye of two or more individuals before eye surgery; measuring the position of the IOL in the eye of two or more individuals after surgery (i.e. eye-operated individuals); and calculating the numerical constant (C) using the formula described above (i.e. $C = (IOL_{measured} - ACD_{pre})/LT$).

Preferably, measuring the position of the crystalline lens in the eye of the two or more individuals before eye surgery is performed measuring the Anterior Chamber Depth of the eye before surgery (i.e. the pre-operative ACD); and measuring the intraocular lens position in the eye of the eye-operated individual after surgery is performed by measuring the Anterior Chamber Depth of the eye after surgery (i.e. the post-operative ACD). Methods for making such measurements are known in the art and are described herein.

As discussed above, the pre-operative ACD is a measurement of the distance from the corneal surface of the eye to the anterior surface of the crystalline lens. It will be appreciated that the position of the crystalline lens could be determined in other ways, based on other measurements of the eye, which would still allow the constant (C) to be calculated. For example, the position of the crystalline lens could be determined by measuring the distance from the corneal surface of the eye to the posterior surface of the crystalline lens (i.e. the pre-operative ACD). Alternatively, the position of the crystalline lens could be determined by measuring the distance from the retinal surface to the anterior or the posterior surface of the crystalline lens. As an example, where the position of the crystalline lens is determined by measuring the distance from the retinal surface to the posterior surface of the crystalline lens, the numerical constant (C) is calculated using the following formula:

$$C=(LP_{ant}-IOL_{post})/LT$$

wherein:

$LP_{ant}$ is the measured distance from the retina to the anterior surface of the crystalline lens position in the eye before surgery;

$IOL_{post}$ is the measured distance from the retina to the centre of the intraocular lens;

LT is the thickness of the crystalline lens in the eye before surgery.

As discussed above, preferably the numerical constant (C) is calculated using the formula: $C=(IOL_{measured}-ACD_{pre})/LT$.

More preferably, the numerical constant (C) is an average (i.e. mean) value obtained from the calculations of the two or more eye-operated individuals using the above approach and preferred formula (i.e. $C=(IOL_{measured}-ACD_{pre})/LT$).

The numerical constant (C) may be between 0.0 and 1.0 (which, when expressed as a percentage, will be between 0% to 100%). Those limits describe the extreme situations with an IOL of infinite thickness which fixes itself onto the anterior capsule or the posterior capsule, respectively, without causing a secondary contraction of the empty capsule after surgery—whilst that is an unlikely situation, the method of the present invention would still work because it would still correctly describes the relationship of the IOL with the anatomical structure of the eye.

Accordingly, it is preferred that the numerical constant (C) is, or is about: 0.1 or 0.2 or 0.3, or 0.4 or 0.5 or 0.6 or 0.7 or 0.8 or 0.9 or 1.0 (which, when expressed as a percentage is: 10% or 20% or 30% or 40% or 50% or 60% or 70% or 80% or 90% or 100%).

It is particularly preferred that the numerical constant (C) is between 0.3 and 0.6; for example, 0.3 or 0.4 or 0.5 or 0.6. Even more preferably, the numerical constant (C) is, or is about, 0.4 (which, when expressed as a percentage, is, or is about, 40%). For example, as shown in the accompanying examples, the numerical constant C, may be 0.387 (i.e. 38.7%).

It will be appreciated that when the IOL design is changed as a result of new developments, and/or when the surgical technique for implanting intraocular lenses is changed, it may change the average post-operative position of an IOL in an eye after surgery. In those instances it may be necessary to study the surgical outcome of a number of eye-operated individuals in order to have a statistically-reliable estimate of the average intraocular lens position.

In those instances, the numerical constant (C) can be continuously adjusted to reflect any changes in intraocular lens design and/or surgical techniques, using the preferred formula above (i.e. $C=(IOL_{measured}-ACD_{pre})/LT$. With a sufficient number of eye-operated individuals, the adjusted value of "C" can be determined with sufficient accuracy to be used prospectively for the new intraocular lens design and/or surgical technique.

Preferably, the invention provides a method wherein step (i) comprises measuring the Anterior Chamber Depth of the pre-operative eye of the patient.

By "Anterior Chamber Depth" or "ACD" we include the distance from the corneal surface to the anterior surface of the lens, whether a natural or an artificial intraocular lens. As used herein, the term "$ACD_{pre}$" refers to the anterior chamber depth of a pre-operative eye as defined herein; whilst the term "$ACD_{post}$" refers to the anterior chamber depth of a post-operative eye as defined herein. Techniques for measuring ACD are well known in the art and include: laser interferometry; ultrasound A-scan; ultrasound B-scan; X-ray scan; CT-scan; MR-scan.

In a preferred embodiment, measuring the Anterior Chamber Depth of the pre-operative eye of the patient is often done with the use of ultrasound. What is measured by ultrasound is the transit time for ultrasound to travel from the corneal surface to the anterior surface of the lens where the beam is reflected. As is the case for the measurement of the axial length (discussed below) there are some disadvantages of this technique, including the possible indentation of the cornea during measurement and uncertainty regarding the velocity of ultrasound assumed for the conversion of transit time to distance.

In another embodiment, measuring the Anterior Chamber Depth of the pre-operative eye of the patient comprises the use of an optical technique selected from the group consisting or comprising of: visible depth measurement; optical coherence tomography; interferometry; partial interferometry; low coherence interferometry; Scheimpflug imaging; laser interferometry; laser biometry.

Optical techniques include measurement of the visible depth of the anterior chamber as seen in the slit lamp (a common tool to perform biomicroscopy of the eye), and more recently measurements using interferometry (Haag-Streit LS900 Lenstar©) or Scheimpflug imaging of the anterior segment of the eye (example of manufacturers: Pentacam© by Oculus Inc, Germany, Galilei© by Ziemer Inc, Switzerland or Sirius© by CSO, Italy). These methods may be regarded as more reliable than ultrasound as they do not need to touch the eye and use optical principles for the distance measurements.

Step (ii) of the method of the first aspect of the invention requires the thickness of the crystalline lens in the pre-operative eye of the patient to be determined, and several methods for doing so are known in the art.

In one embodiment, determining lens thickness comprises the use of ultrasound. Methods for determining lens thickness using ultrasound are well known to those skilled in the art. Using that technique, what is measured is the transit time for ultrasound to travel from the front surface of the lens to the posterior surface of the lens. That technique does have some limitations and disadvantages that need to be considered—for example, the cataractous lens may not be an acoustically-homogenous medium, and the occurrence of intra-lenticular echoes from lens opacities may blur the signal from the posterior capsule of the lens. Another uncertainty is related to the assumed velocity of ultrasound used to convert transit time to distance.

In an alternative embodiment, the thickness of the crystalline lens in the pre-operative eye of the patient in step (ii) is determined using laser interferometry or laser biometry.

Recently, laser interferometry has been used to measure the thickness of the lens (for example, using a Haag-Streit LS900 Lenstar©). That technique appears much more accurate than ultrasound and seems to be less prone to errors arising from in-homogenous lens matter.

It is particularly preferred that predicting the post-operative position of the intraocular lens in step (iii) comprises the use of the formula:

$$IOL_{predicted} = ACD_{pre} + C \times LT$$

wherein:
$IOL_{predicted}$ is the predicted post-operative position of the intraocular lens in the eye of the patient;
$ACD_{pre}$ is the pre-operative Anterior Chamber Depth of the eye of the patient;
C is a numerical constant, as discussed above; and
LT is the thickness of the crystalline lens in the pre-operative eye of the patient.

Thus, a particularly preferred embodiment of the method of the first aspect of the invention comprises: a method for predicting the post-operative position of a replacement IOL in an eye of a patient, comprising the steps of:
(i) determining the position of the existing crystalline lens in the pre-operative eye of the patient;
(ii) determining the thickness of the crystalline lens in the pre-operative eye of the patient; and
(iii) predicting the post-operative position of the IOL using the formula:

$$IOL_{predicted} = ACD_{pre} + C \times LT$$

wherein:
$IOL_{predicted}$ is the predicted post-operative position of the IOL in the eye of the patient;
$ACD_{pre}$ is the pre-operative Anterior Chamber Depth of the eye of the patient;
C is a numerical constant, as discussed above; and
LT is the thickness of the lens in the pre-operative eye of the patient.

It is preferred that $IOL_{measured}$ is the position to the centre of the intraocular lens.

In a second aspect, the invention provides a method for selecting a replacement IOL required to provide a desired optical property in a post-operative eye of a patient, the method comprising the steps of:
(a) predicting the post-operative position of a replacement IOL in the eye of the patient using a method according to the first aspect of the invention;
(b) predicting the optical properties of the post-operative eye of the patient in which an IOL of known power and geometry is positioned as predicted in step (a); and
(c) selecting an IOL having a power and geometry required to provide the desired optical property in the post-operative eye of the patient.

Of course, the desired outcome of eye surgery is to provide for the patient an aberration-free optical system which gives the best focus with minimal blur.

As is known in the art, the majority of "eye defects" that can be corrected by an IOL include the spherical and cylindrical dioptric power of the IOL which is a direct correlate of the spherical and cylindrical correction used in spectacles. For multifocal IOLs there will also be an 'add' power related to the additional power needed for near vision ('reading addition').

These basic dioptric eye defects are described by the spherical and cylindrical spectacle correction needed to give the best visual acuity. This examination is a routine examination performed by an optician, optometrist or an eye doctor. The visual acuity refers to the highest visual resolution that can be perceived, that is 'the smallest letters discernible'. In physical optics this correlates to the 'point-spread function' or 'modulation transfer function' that characterizes an optical instrument. Ideally speaking, a point should be imaged as a point, but often this is not the case and then there will be a certain spread around the peak signal.

As is known in the art, the remaining optical "eye defects" are termed "higher order aberrations" such as: coma, tilt, Petzval field curvature, distortion and chromatic aberration. As described in textbooks on the physical optics (such as Born & Wolf; "Principles of Optics", $6^{th}$ edition, Pergamon Press, New York, 1980; and Bennett& Rabbetts; Clinical Visual Optics, Butterworth, London), many theoretical models are available to describe optical aberrations, including Wavefront technology, Zernike polynomials, and Fourier transformation. Zernike polynomials use numerous coefficients to characterize the individual "defects" of the entire optical system.

The optical defects of the cornea can be measured by instruments like corneal topography or tomography. The optical defect of the eye as a whole can be measured by clinical instruments using wavefront aberrometry which will give numbers for all of the higher order aberrations according to the Zernike model or other models. The optical defects of the lens can be measured by subtracting the corneal defects from the total eye defects. In this way it is possible to measure the aberrations of the IOL within the eye.

Once a desired optical property has been identified in a patient, a suitable intraocular lens can be selected. It will be appreciated that intraocular lenses can have a range of properties. Most manufacturers produce IOLs with a label stating the "dioptric power" of the IOL. By ANSII definition this relates to the thickness, the refractive index and the curvatures of the central part of the IOL.

As discussed above, the majority of eye defects that can be corrected by an IOL include the spherical and cylindrical dioptric power of the IOL which is a direct correlate of the spherical and cylindrical correction used in spectacles. For multifocal IOLs there will also be an 'add' power related to the additional power needed for near vision ('reading addition').

However, optical properties comprise more than just dioptric power of the paraxial region of the IOL. During the last decade, many IOLs were also produced with a correction of the spherical aberration that is found in the human eye—more specifically, this relates to the Z(4) term of the Zernike polynomial, which is known in the art. The amount of the correction is often stated in micrometers (μm)—for example, 0.21 μm) referring to a wavefront correction for a given pupil size. The amount of asphericity varies however. Some IOLs have been manufactured to try to correct all of the natural spherical aberration while others seek only to correct a part of it. Instruments for performing 'Wavefront analysis' of the eye to provide a Zernike analysis of the optics of the eye are known in the art.

Thus, a particularly preferred embodiment of the method of the second aspect of the invention comprises: a method for selecting a replacement IOL required to provide a desired optical property in a post-operative eye of a patient, the method comprising the steps of:
(a) predicting the post-operative position of a replacement IOL in the eye of the patient by a method comprising the steps of:
(i) determining the position of the existing crystalline lens in the pre-operative eye of the patient;
(ii) determining the thickness of the crystalline lens in the pre-operative eye of the patient; and (iii) predicting the post-operative position of the IOL using the formula:

$$IOL_{predicted} = ACD_{pre} + C \times LT$$

wherein:
   $IOL_{predicted}$ is the predicted post-operative position of the IOL in the eye of the patient;
   $ACD_{pre}$ is the pre-operative Anterior Chamber Depth of the eye of the patient;
   C is a numerical constant, as discussed above; and
   LT is the thickness of the crystalline lens in the pre-operative eye of the patient;
(b) predicting the optical properties of the post-operative eye of the patient in which an IOL of known power and geometry is positioned as predicted in step (a); and
(c) selecting an IOL having a power and geometry required to provide the desired optical property in the post-operative eye of the patient.

Step (b) of the method of the second aspect of the invention comprises predicting the optical properties of the post-operative eye of the patient in which an IOL of known power and geometry is positioned as predicted in step (a).

Preferably, predicting the optical properties of the post-operative eye of the patient comprises establishing an optical model of the post-operative eye of the patient. Optical modelling techniques are known in the art and typically involve establishing a model of the eye of the patient based on measurements of its optical properties and dimensions (which are, conveniently, taken prior to surgery). Numerous approaches for establishing and analysing such models are known in the art, as discussed in more detail below.

In a preferred embodiment, the optical model of the post-operative eye of the patient comprises measuring the curvatures of the cornea of the pre-operative eye of the patient (for example, by keratometry, topography or tomography, as discussed herein) and the axial length of the pre-operative eye of the patient (for example, by ultrasound or laser biometry, as discussed herein).

Once a model for the eye of the patient has been established, the refraction of light within that eye can be analysed and a prediction made of the optical properties when an intraocular lens of known power and geometry is positioned within it. Such modelling and predictions allow an intraocular lens to be selected which has the necessary spherical and cylindrical dioptric power and other optical property that are required to provide the desired optical property in the post-operative eye of the patient.

As discussed above, when light passes through the ocular media it is deflected at a number of interfaces following the physical principles of refraction such as Snell's law. However, in order to apply the physical principles correctly to the biological structure it is crucial that the clinical measurements accurately reflect the physical dimensions and furthermore, that the perception of the image is closely related to the formation of the image on the retina.

It is preferred that the model of the eye of the patient used in the methods of the invention (such as in steps (b) and (c) of the method of the second aspect of the invention) contains at least one of the following surfaces and/or interfaces: the anterior cornea surface; the posterior cornea surface; the anterior lens surface of the biological lens; the posterior lens surface of the biological lens; the IOL anterior surface; the IOL posterior surface; the retina.

Axial Length

As is well known, a crucial parameter for a correct model of the eye is the axial length of the eye. Axial length needs to be measured with a high accuracy—an error of just 1 mm in the axial length transposes into a 2.5 D error in the spectacle plane in the average eye.

Various clinical methods exist for measuring the axial length, such as ultrasound and partial coherence interferometry.

Axial length has traditionally been measured by ultrasound using so-called 'A-scan'. What is actually measured is the transit time of ultrasound as it travels through the ocular media and reflects at the internal boundaries of the eye. Assuming a known velocity of ultrasound in the different ocular compartments (cornea, anterior chamber, lens and vitreous compartment), it is possible to calculate the distance from the cornea to the acoustically-reflecting membrane at the back of the eye.

As is well known, there are a number of uncertainties in the measurement of the axial length by ultrasound. Firstly, all the velocity of ultrasound has to be accurate for the different ocular media, which may not always be the case considering the varying cataract density seen in clinical practice. Secondly, many ultrasound techniques use applanation of the cornea to transmit the ultrasound to the eye and this may cause indentation of the cornea during measurement and shortening of the reading. Thirdly, ultrasound measures the distance to the reflecting membrane at the back surface of the eye (presumably the internal limiting membrane constituting the boundary between the vitreous cavity and the nerve fibre layer of the retina), which is not identical to the position of the light-absorbing retinal photoreceptors of the eye.

The fact that there is an intrinsic error of the ultrasound measurement due to the difference between point of measurement and the position of the effective focal plane at the retina (=the photoreceptors), has led many intraocular lens power calculation formulas to incorporate a corrective term called 'the retinal thickness', typically around 0.25 mm.

In recent years, the introduction of laser biometry using partial coherence interferometry (termed "PCI") (Drexler et al., 1998) has significantly improved the accuracy by which the axial length can be measured. The PCI technique has been made commercially available as the IOLMaster© instrument made by Carl Zeiss Meditec©, Jena, Germany.

The wavelength of light is much shorter than that of sound which greatly improves the physical resolution. While typical precision values with good ultrasound measurements are stated to be within ±0.1 mm, the precision with PCI is stated to be approximately ten-fold better (i.e. within ±0.01 mm) and it is independent on the observer (Connors, III et al., 2002; Find) et al., 2003; Haigis, 2001; Kiss et al., 2002; Packer et al., 2002; Vogel et al., 2001). Furthermore, the fact that the retinal pigment epithelium is the end-point of optical measurement makes the measurements by the PCI technique optically more correct (and longer than that of ultrasound).

However, just like measurements using ultrasound are dependent on the assumed ultrasound velocity, optical biometry is dependent on the assumed group refractive indices of the phakic eye. The indices used by the Zeiss IOLMaster© were estimated by Haigis (Haigis, 2001), partly based on extrapolated data. As shown subsequently however, the index calibration of the phakic eye may need adjustment to give consistent readings between the pre-operative and the post-operative readings (Olsen and Thorwest, 2005a).

For an accurate interpretation of the axial length reading of the Zeiss IOLMaster© it should be realised that the output reading of that instrument is not the true optical path length of the eye—that is, it is not the true axial length. In order not to change the world of A-constants and other formula constants used for years with ultrasound, the readings given by the commercial version of the Zeiss IOLMaster© were calibrated against immersion ultrasound according to the following formulae (Haigis et al., 2000; Haigis, 2001):

$$AxZeiss=(OPL/1,3549-1,3033)/0,9571$$

wherein:
AxZeiss is the output reading of the Zeiss instrument; and
OPL is the optical path length measured by PCI.
Thus:

$$OPL=(AxZeiss*0,9571+1,3033)*1,3549$$

Assuming a refractive index of 1.3574 for the phakic eye (Haigis, 2001):

$$Axtrue=(AxZeiss*0.9571+1.3033)*1.3549/1.3574$$

According to Olsen (Olsen and Thorwest, 2005b) the refractive index of 1.3574 for the phakic eye may not be the best choice. A better value which will give consistent pre- and postoperative readings may be to use a higher index such as 1.3616. The true axial length from the Zeiss reading can therefore be calculated as:

$$Axtrue=(AxZeiss*0.9571+1.3033)*1.3549/1.3616$$

This conversion is preferably used in the methods of the present invention. (However, it is possible the index calibration may be adjusting as we gain more experience on laser biometry)

Preferably, the axial length of an eye is measured by means of interferometry, preferably by means of a low coherence interferometry instrument or partial coherence interferometry instrument (such as a Carl Zeiss MeditecI-OLMaster or Haag-Streit LS900 Lenstar).

Optical Properties of the Cornea

The radius of the anterior surface of the cornea is preferably measured by means of keratometry and/or by means of corneal topography. It is furthermore assumed that the radius of the posterior surface of the cornea is a fixed ratio of the radius of the anterior surface of the cornea. The radius of the posterior surface of the cornea is preferably assumed to 0.84 times the radius of the anterior surface of the cornea.

A correct model of the eye is only provided if the asphericity of the corneal surfaces is also accounted for. The asphericity of the posterior corneal surface is preferably assumed to be linearly dependent on the anterior surface and the asphericity of the posterior and the anterior corneal surfaces are preferably assumed to be depending on the age of the patient. According to Dubbelman et al., 2006 the asphericity of the anterior corneal surface is preferably assumed to be 0.76 plus 0.003 times the age of the patient, and the asphericity of the posterior corneal surface is preferably assumed to be 0.76 plus 0.325 times the asphericity of the anterior corneal surface minus 0.0072 times the age of the patient.

Spherical aberration is a phenomenon of many lenses including the cornea and non-aspheric IOLs where peripheral rays are refracted differently from central rays. The human eye has a certain amount of positive spherical aberration which accounts for the 'night myopia' that many people experience at mesopic (dim light) conditions where the pupil becomes large.

Spherical aberration is corrected somewhat by the so-called Stiles-Crawford effect, whereby the retinal sensitivity is depending on the angle by which the rays hit the retina. The Stiles-Crawford effect predicts the retinal sensitivity to be at a maximum for rays entering the pupil centre and to be of less efficiency for rays entering the pupil edge. The consequence of the Stiles-Crawford effect is that it tends to correct for the effect of spherical aberration when the pupil becomes large (Olsen 1993).

Preferably, the IOL power is corrected for spherical aberration, preferably by means of the Stiles Crawford effect $I=I_0 exp(-C*\gamma^2)$, where C is a numerical constant and γ is the distance from the centre of the pupil. C is preferably 0.108 when γ is measured in millimeters (mm).

The refractive power of the cornea is usually provided by measuring the curvature of the front surface of the cornea by an instrument called the 'keratometer'. What is actually measured is the magnification of the convex mirror constituted by the anterior reflecting surface of the eye. This is converted into radius assuming the central portion of the cornea is spherical. When the keratometer reports the dioptric 'power' of the cornea it does so by assuming the cornea is a 'thin lens' with a single refracting surface of power:

$$F = \frac{n_2 - n_1}{r}$$

wherein:
F=refractive power of surface in dioptres;
r=radius of curvature in meters;
$n_1$=refractive index of first media (air); and
$n_2$=refractive index of second media (cornea).

The conventional calibration of clinical keratometers assumes the refractive index of the single-surfaced cornea to be 1.3375, giving the equation:

$$D=337.5/r$$

wherein:
D=power of the cornea in dioptres; and
r=radius of curvature in millimeters.

As shown in Olsen, 1986a, the refractive index calibration of 1.3375 is not accurate from a more physiological, 'thick lens' theory, which predicts the corneal power about 0.75 D lower in the average case depending on the corneal model. This 'inborn error' of the common keratometer reading is important from a physical point of view because if not corrected for, it will induce an error in all subsequent calculations and eventually require a correction at the end to work in an intraocular lens power formula.

Another problem deals with the topographical variation in corneal radius that may be found not only in normal corneas but especially in corneas that have had previous refractive surgery (PRK, LASIK, LASEK and other laser ablation procedures with the aim to correct the refractive error by changing the curvature of the anterior surface). In such post-LASIK corneas the shape of the anterior surface is far from spherical, and may need to be evaluated using corneal topography measuring the curvature in numerous points of the entire corneal surface.

In order to treat the cornea as a 'thick lens' the corneal thickness and the curvature of the posterior surface also need to be taken into consideration. In most corneal models the posterior curvature is assumed to be a fixed ratio of the anterior curvature assuming a standard corneal shape. For many years the standard shape and hence the radius of the posterior surface was assumed to be as proposed by Gullstrand (Gullstrand, 1924). However, it is not until recently that more modern studies have provided detailed information not only on the curvatures of both surfaces of the cornea, but also on their asphericity (Dunne et al., 1992; Dubbelman et al., 2002; Dubbelman et al., 2006). These findings have improved the conditions to build more realistic models for the optics of the cornea and hence the entire ocular optics.

The refractive index of the cornea is assumed to be a constant value of 1.376 and the thickness of the cornea is assumed to be a constant value of 0.5 mm. The anterior curvature is assumed to be measured using conventional keratometry and/or by corneal topography. The radius reading is used rather than the dioptre reading to avoid confusion from the keratometer index problem.

When the posterior curvature of the cornea is not measured directly, the posterior surface of the cornea is generally assumed to be a fixed ratio of the anterior surface. According to the model described by Dubbelman (Dubbelman et al., 2002) this ratio is:

$$R_2 = 0.84 * R_1$$

wherein:
$R_2$=radius of posterior surface of the cornea; and
$R_1$=radius of anterior surface of the cornea.

Also from the work of Dubbelman (Dubbelman et al., 2002) the asphericity of the corneal surfaces is assumed to be depending on the age of the patient according to the following equations:

$$K_a = 0.76 + 0.003 * Age.$$

$$K_p = 0.76 + 0.325 * K_a - 0.0072 * Age$$

wherein:
$K_a$=asphericity of the anterior surface of the cornea;
$K_p$=asphericity of the posterior surface of the cornea; and
Age=age of the patient in years.

The Dubbelman model used here predicting the posterior central curvature of the cornea to be 84% of the anterior curvature differs somewhat from the previous Gullstrand ratio of 6.8/7.7 (88.3%) used by Olsen in the original 'thick lens' formula. If not for the asphericity this would mean the corneal power to be lower than previously assumed. However, when the asphericity of the cornea is also taken into account (by exact ray-tracing) the effective power of the cornea has been shown to be somewhat higher than that predicted by the Gullstrand ratio (Olsen, 2007).

Methods for measuring the Anterior Chamber Depth in a pre-operative and a post-operative eye, and the thickness of natural, biological crystalline lenses and artificial lenses are discussed above.

Properties of the Intraocular Lens

In order to predict the optical outcome of an intraocular lens to be implanted, it is crucial to know the power and geometry of the intraocular lens. Intraocular lens manufacturers typically provide data for the refractive index and the thickness and the curvatures of the front and back surfaces of the intraocular lens, and the power and geometry are preferably calculated from these data.

The physical description of the intraocular lens studied in the accompanying Examples was based on the manufacturer's data on the refractive index, the thickness and curvatures of front and back surfaces of the intraocular lens. The surface curvatures vary according to the power of the implant so it was necessary to use tabulated values of the physical data as a function of labelled power.

By definition (ANSI-standard), the labelled power of an intraocular lens refers to the paraxial curvatures of the lens, its thickness and refractive index. In the case of a spherical intraocular lens the curvature is constant over the entire area. In the case of an aspheric intraocular lens the curvature is depending on the asphericity and varies from the central to the peripheral parts of the lens.

In order to evaluate the result of a ray tracing analysis and thereby assess the optical properties of an eye, at least one point spread function is preferably calculated and evaluated at the retina of the eye and/or at the point of best focus.

As an example of the modelling that is possible using the methods and instrumentation discussed above is shown in FIGS. 3 and 4.

Figure 3:
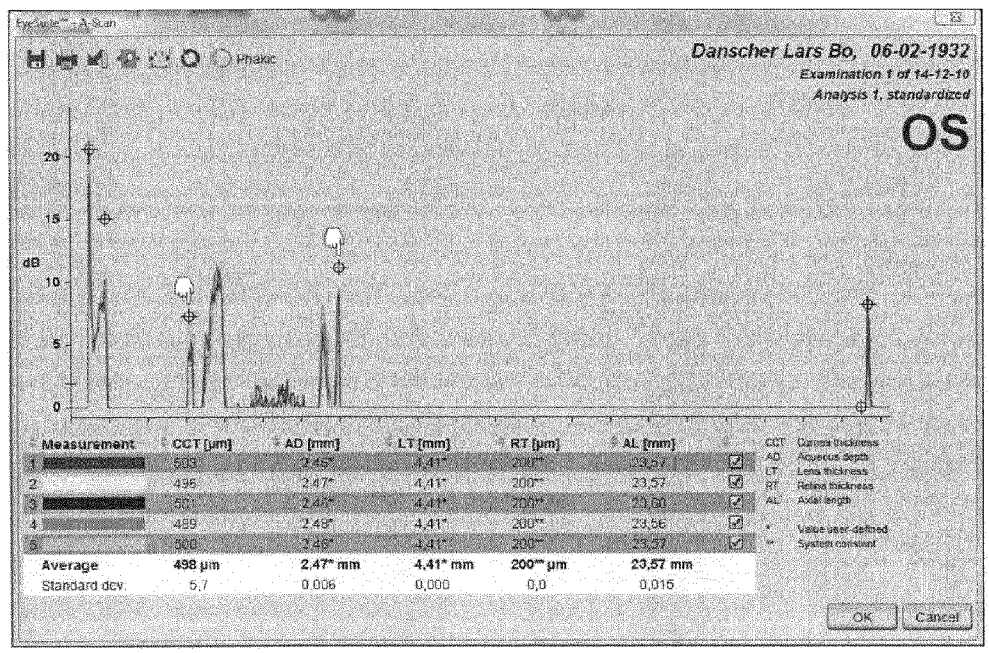

FIG. 3 shows an example of an optical scan of a phakic eye performed using the Haag-Streit Lenstar biometer, which demonstrates its accuracy in determining various parameters of the phakic eye, including lens thickness (pointing hands in Figure). Usually a series of measurements is taken, each one showing the intraocular dimensions (from left to right in the Figure) of the central corneal thickness ("CCT" in the Figure), the anterior chamber depth ("AD" in the Figure), the lens thickness ("LT" in the Figure) and the total axial length ("AL" in the Figure). At the bottom of the Figure is shown the variation between the individual readings. Because of the interferometry technique used, the standard deviation is generally very low meaning a high precision of the measurements.

Figure 4:
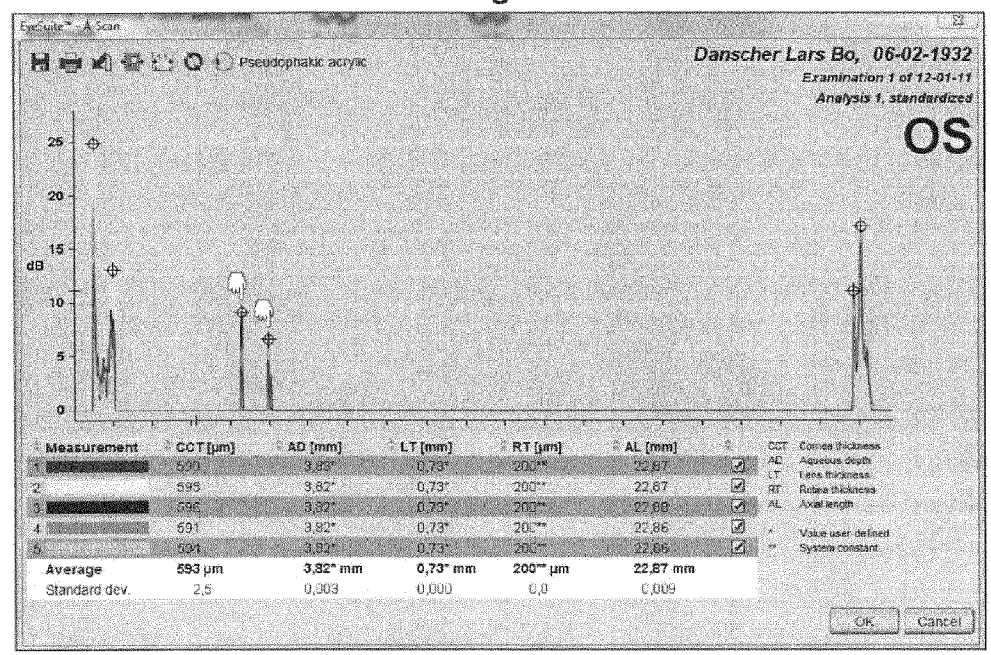

FIG. 4 shows an example of a post-operative scan of the same eye shown in FIG. 3, one day after surgery. The natural crystalline lens has been replaced by an intraocular lens positioned within the capsular bag. The position of the intraocular lens is often readily detected and measurable (pointing hands in figure).

It will be appreciated that, in order to select an appropriate IOL for implantation into the eye of a patient, a realistic optical model of that eye is needed.

Preferably, the second aspect of the invention provides a method wherein establishing an optical model of the post-operative eye of the patient comprises measuring one or more property of the pre-operative eye of the eye of the patient, selected from the group consisting of: the optics of the cornea; the corneal radius; the length of the eye; the axial length; the anterior chamber depth; the crystalline lens thickness.

Most preferably, the axial length of the eye and the curvature of the anterior surface of the cornea of the eye are measured. These data are used for input into the IOL power calculation formulas which are known in the art.

It will be appreciated that, in some cases it may be necessary to apply further analysis to study the corneal shape. For example, if a patient has undergone LASIK surgery prior to lens surgery, the anterior surface of this patient is changed which disrupts the standard models to calculate the corneal power from anterior surface data only. In those instances it may be necessary to measure the posterior curvature of the cornea as well and this can be done using modern high-definition scanning techniques.

Preferably, step (b) of the method of the second aspect of the invention further comprises analysing the optical properties of the optical model of the post-operative eye of the patient.

For many years, 'the Olsen Formula' has been used, which has been a so-called 'thick-lens' IOL power formula using the well-known theory from Gaussian Optics which is so-called paraxial ray tracing. The advantage of using a 'thick-lens' model is that it allows you to use the distances as they can be measured assuming no higher-order aberrations. That is in contrast to a 'thin-lens' model where the effective lens planes (ELP) are reduced to imaginary planes close, but not identical, to the measured ones.

Recently, a more sophisticated model using exact ray tracing has been described (in WO 2010/028654) and that model has the advantage that it uses as few assumptions as possible and it allows optical theory to be applied from the physical world to the human eye. Using that approach, it is possible to analyse higher-order aberrations (like spherical aberration) and other properties that are not handled by a 'thick-lens' model.

In a particularly preferred embodiment, analysing the optical properties of the optical model of the post-operative eye of the patient comprises the use of exact ray tracing analysis. Such approaches are discussed herein and in are known in the art (as discussed, for example, in WO 2010/028654).

In an alternative embodiment, analysing the optical properties of the optical model of the post-operative eye of the patient comprises the use of paraxial ray tracing analysis. Such approaches are discussed herein and in are known in the art (as discussed, for example, in WO 2010/028654).

Ray tracing is well known in the art as a method for simulating the optical properties of the eye, which is based on Snell's law of refraction:

$$\text{Sin } \theta_1 / \text{Sin } \theta_2 = n_2/n_1$$

wherein:
$\theta_1$=angle of incidence of incoming light in first media;
$\theta_2$=angle of refracted light in second media;
$n_1$=refractive index of first media; and
$n_2$=refractive index of second media.

In brief, by knowing the curvatures of each surface of a given optical system it is possible to simulate the imagery by 'firing' a number of rays through the system and observe the distribution of the rays at the image plane. For the purposes of the present invention, where ray tracing analysis is used it assumes rotational symmetry of the individual surfaces and assumes the rays are equally distributed over the area of the entrance aperture. The mathematics involved in the ray tracing methodology are well known from optical engineering and involves the description of ellipses and conicoid sections (Baker, 1943). An illustration of how ray tracing can be performed is described in the accompanying Examples.

It will be appreciated that the improved predictions of post-operative IOL position provided by the present invention mean that patients could be identified for whom an IOL with suitable optical properties is not available. In those cases, such patients would require an IOL to be custom-designed and made with optical properties suitable for their eyes.

Accordingly, in a third aspect, the invention provides a method for designing a replacement intraocular lens required to provide a desired optical property in the post-operative eye of the patient, the method comprising the steps of:
(a1) predicting the post-operative position of a replacement intraocular lens in the eye of the patient using a method according to the first aspect of the invention;
(b1) predicting the optical properties of the post-operative eye of the patient in which an intraocular lens of known power and geometry is positioned as predicted in step (a);
(c1) designing an intraocular lens having a power and geometry required to provide the desired optical property in the post-operative eye of the patient;
(d1) optionally, manufacturing the intraocular lens designed in step (c1).

Thus, a particularly preferred embodiment of the method of the third aspect of the invention comprises: a method for designing a replacement intraocular lens required to provide a desired optical property in the post-operative eye of the patient, the method comprising the steps of:
(a1) predicting the post-operative position of a replacement intraocular lens in the eye of the patient using a method comprising the steps of:
(i) determining the position of the existing crystalline lens in the pre-operative eye of the patient;
(ii) determining the thickness of the crystalline lens in the pre-operative eye of the patient; and
(iii) predicting the post-operative position of the IOL using the formula:

$$\text{IOL}_{predicted} = \text{ACD}_{pre} + C \times \text{LT}$$

wherein:
$\text{IOL}_{predicted}$ is the predicted post-operative position of the intraocular lens in the eye of the patient;
$\text{ACD}_{pre}$ is the pre-operative Anterior Chamber Depth of the eye of the patient;
C is a numerical constant, as discussed above; and
LT is the thickness of the crystalline lens in the pre-operative eye of the patient;
(b1) predicting the optical properties of the post-operative eye of the patient in which an intraocular lens of known power and geometry is positioned as predicted in step (a1);
(c1) designing an intraocular lens having a power and geometry required to provide the desired optical property in the post-operative eye of the patient;
(d1) optionally, manufacturing the intraocular lens designed in step (c1).

Preferably, step (b1) of the method of the third aspect of the invention is performed as discussed above in relation to the second aspect of the invention.

Thus, preferably step (b1) comprises establishing an optical model of the post-operative eye of the patient. Optical modelling techniques are known in the art and typically involve establishing a model of the eye of the patient based on measurements of its optical properties and dimensions (which can, conveniently, be taken prior to surgery). Once a model for the eye of the patient has been established, the refraction of light within that eye can be analysed and a prediction made of the optical properties when an intraocular lens of known power and geometry is positioned within it. Such modelling and predictions allow an intraocular lens to be selected which has the necessary power and geometry that are required to provide the desired optical property in the post-operative eye of the patient.

Preferably, establishing an optical model of the post-operative eye of the patient comprises measuring one or more property of the pre-operative eye of the eye of the patient, selected from the group consisting of: the optics of the cornea; the corneal radius; the length of the eye; the axial length; the anterior chamber depth; the crystalline lens thickness.

Conveniently, step (b1) further comprises analysing the optical properties of the optical model of the post-operative eye of the patient—preferably, such analysis comprises the use of exact ray tracing analysis or paraxial ray tracing analysis. Such approaches are discussed above in relation to the second aspect of the invention.

Methods for designing and manufacturing IOLs are well known to those in the art, and are discussed, for example in Born & Wolf ("Principles of Optics", 6$^{th}$ edition, Pergamon Press, New York, 1980) and Bennett & Rabbetts (Clinical Visual Optics, Butterworth, London).

IOLs are manufactured from materials that have been proven over many years to be tolerated by the eye, and are made according to current optical manufacturing standards (within certain tolerances). There are ANSII standards on the accepted tolerances on power. In the industry, optical properties of IOLs are often determined on an "optical bench" to measure back focal length and the so-called point-spread function or the so-called modulation transfer function (MTF). In optical engineering, a widely-used software program is ZEMAX, which can perform detailed optical analysis of any optical structure (including the eye) given the physical information.

Preferably, the designed in step (c1) and/or manufactured in step (d1) is adapted for implantation into the capsular bag of the eye of a patient. Features of such IOLs, and methods for performing implantation into the capsular bag, are discussed above and are known in the art.

In a fourth aspect, the invention provides a method for implanting a replacement intraocular lens into an eye of a patient, the method comprising the steps of:
- (a2) predicting the post-operative position of the replacement intraocular lens in the eye of the patient using a method according to the first aspect of the invention;
- (b2) optionally, removing the existing crystalline lens from the pre-operative eye of the patient;
- (c2) providing an intraocular lens;
- (d2) implanting the intraocular lens into the eye of the patient.

Thus, a particularly preferred embodiment of the method of the fourth aspect of the invention comprises: a method for implanting a replacement intraocular lens into an eye of a patient, the method comprising the steps of:
- (a2) predicting the post-operative position of the replacement intraocular lens in the eye of the patient using a method comprising the steps of:
  - (i) determining the position of the existing crystalline lens in the pre-operative eye of the patient;
  - (ii) determining the thickness of the crystalline lens in the pre-operative eye of the patient; and
  - (iii) predicting the post-operative position of the IOL using the formula:

$$IOL_{predicted} = ACD_{pre} + C \times LT$$

wherein:
  $IOL_{predicted}$ is the predicted post-operative position of the intraocular lens in the eye of the patient;
  $ACD_{pre}$ is the pre-operative Anterior Chamber Depth of the eye of the patient;
  C is a numerical constant, as discussed above; and
  LT is the thickness of the crystalline lens in the pre-operative eye of the patient;
- (b2) optionally, removing the crystalline lens from the pre-operative eye of the patient;
- (c2) providing an intraocular lens;
- (d2) implanting the intraocular lens into the eye of the patient.

It will be appreciated that removing the crystalline lens from the pre-operative eye of the patient in step (b2) will not be necessary if the crystalline lens is not present (for example, due to being damaged or destroyed by disease or disorder).

In one embodiment, the intraocular lens provided in step (c2) of the method of the fourth aspect of the invention is selected using a method according to the second aspect of the invention.

In an alternative embodiment, the intraocular lens provided in step (c2) of the method of the fourth aspect of the invention is designed, and optionally manufactured, using a method according to the third aspect of the invention.

Preferably, the IOL provided in step (c2) is adapted for implantation into the capsular bag of the eye of a patient. Preferably, step (d2) comprises implanting the intraocular lens into the capsular bag in the eye of the patient. Methods suitable for implanting an intraocular lens into an eye of a patient are well known in the art and are described herein.

It will be appreciated that the methods of the present invention may be used when implanting an IOL into the eye of a patient that is suffering from a disorder and/or disease of the eye, and that implantation of the IOL results in the treatment and/or prevention and/or reduction in that disease or disorder.

Thus, in a fifth aspect, the invention provides a method for treating and/or preventing and/or reducing a disease or disorder in the eye of a patient, the method comprising the steps of:
- (a3) predicting the post-operative position of a replacement intraocular lens in the eye of the patient using a method according to the first aspect of the invention;
- (b3) optionally, removing the existing crystalline lens from the pre-operative eye of the patient;
- (c3) providing an intraocular lens;
- (d3) implanting the intraocular lens into the eye of the patient.

It will be appreciated that removing the crystalline lens from the pre-operative eye of the patient in step (b3) will not be necessary if the crystalline lens is not present (for example, due to being damaged or destroyed by disease or disorder).

Thus, a particularly preferred embodiment of the method of the fifth aspect of the invention comprises: a method for treating and/or preventing and/or reducing a disease or disorder in the eye of a patient, the method comprising the steps of:
- (a3) predicting the post-operative position of a replacement intraocular lens in the eye of the patient using a method comprising the steps of:
  - (i) determining the position of the existing crystalline lens in the pre-operative eye of the patient;
  - (ii) determining the thickness of the crystalline lens in the pre-operative eye of the patient; and
  - (iii) predicting the post-operative position of the IOL using the formula:

$$IOL_{predicted} = ACD_{pre} + C \times LT$$

wherein:
  $IOL_{predicted}$ is the predicted post-operative position of the intraocular lens in the eye of the patient;
  $ACD_{pre}$ is the pre-operative Anterior Chamber Depth of the eye of the patient;
  C is a numerical constant, as discussed above; and
  LT is the thickness of the crystalline lens in the pre-operative eye of the patient;
- (b3) optionally, removing the crystalline lens from the pre-operative eye of the patient;
- (c3) providing an intraocular lens;
- (d3) implanting the intraocular lens into the eye of the patient.

It will be appreciated that removing the crystalline lens from the pre-operative eye of the patient in step (b3) will not be necessary if the crystalline lens is not present (for example, due to being damaged or destroyed by disease or disorder).

In one embodiment, the intraocular lens provided in step (c3) of the method of the fifth aspect of the invention is selected using a method according to the second aspect of the invention.

In an alternative embodiment, the intraocular lens provided in step (c3) of the method of the fifth aspect of the invention is designed, and optionally manufactured, using a method according to the third aspect of the invention.

Preferably, the IOL provided in step (c3) is adapted for implantation into the capsular bag of the eye of a patient. Preferably, step (d3) comprises implanting the intraocular lens into the capsular bag in the eye of the patient. Methods suitable for implanting an intraocular lens into an eye of a patient are well known in the art and are described herein.

Preferably, the disease or disorder in the eye of the patient is selected from the group consisting of: Myopia (i.e. near-sightedness); Hyperopia (i.e. long-sightedness); Presbyopia; Astigmatism; Refractive errors; Cataract; Opacities; Brunescence (i.e. clouding of the lens). Such diseases and disorders are well known, and those skilled in the art will be aware of how to identify such diseases and disorders.

Preferably the patient in the method of the first aspect of the invention and/or the second aspect of the invention and/or the third aspect of the invention and/or the fourth aspect of the invention and/or the fifth aspect of the invention is a mammal, for example a human or a mammal of agricultural or commercial value, such as a mammal selected from the group consisting of: horse; cow; pig; sheep; dog; cat; rabbit. In a preferred embodiment, the patient is a human.

In a sixth aspect, the invention provides a computer program for instructing a computer to perform the method according to the first aspect of the invention and/or the second aspect of the invention and/or the third aspect of the invention and/or the fourth aspect of the invention and/or the fourth aspect of the invention.

Thus, the present invention addresses the problems of the prior art, and provides an improved method for the prediction of the post-operative position of an intraocular lens in the eye of a patient. As discussed above, the present invention is particularly advantageous because it provides a prediction method which is based on a true, physically-defined post-operative position of the intraocular lens position rather than a virtual post-operative position.

Methods used for predicting the position of an intraocular lens prior to surgery, and/or calculating intraocular lens power, that were used before the development of the present invention are discussed below:

Prior Art Methods

The aim of any intraocular lens power calculation formula is to control the optical outcome of lens surgery with the implantation of an intraocular lens.

Many formulas have been described to calculate the intraocular lens power to be used in cataract surgery (for a review, see Olsen 2007 and the section 'Early formulas' below). Most of these formulas have been derived in the following way: based on a simple 'thin lens' model of the optics of the eye, a large series of patients have been analysed for the eventual refractive outcome, and the formula back-solved for the effective lens plane (ELP) in the individual case.

The ELP can be regarded as a virtual distance which—when used in the particular formula with the measured dataset—will produce the observed refractive outcome. By taking the average of a number of cases, an average ELP (or an A-constant in the SRK approach) is derived describing the average value in the population for a given intraocular lens type.

Because all presently available formulas use very simplified models for the optics of the eye they require a number of corrective terms to be calculated in retrospect from observed data in order to work accurately. Examples of these 'fudge' factors include the 'A-constant' (SRK-formula), 'Surgical Factor' (Holladay) or 'effective ELP or ACD' (Hoffer or Binkhorst formula). The 'fudging' procedure ensures that the predictions with the particular formula are accurate in the average case. It does not ensure, however, that the predictions are accurate in the individual case.

Most of the above-mentioned formulae have used only two important input parameters as measured before the operation:

(1) Keratometry (K-reading) of the cornea which is essentially a measurement of the front curvature of the cornea; and
(2) The length of the eye—known as the Axial length which is measured by ultrasound or laser interferometry From these two variables, the formula incorporates a mathematical model for the effective intraocular lens position (ELP). The exact way the K-reading and the axial length are transformed into an individual ELP is embedded in the formula and differs from formula to formula, however.

Conventional IOL Power Calculation Formulae

The first implantation of an artificial lens was performed by Harold Ridley in 1949. However, it was not until the 1970's that the implantation of artificial lenses became common clinical practice and from that time several methods have been described to calculate the dioptric power of the intraocular lens implanted.

The first methods used optical formulae known from the optical-physical theory of 'thin lenses'. These methods were simple formulas based on the assumptions that:

(1) the cornea was a 'thin lens' the power of which could be measured;
(2) the intraocular lens was also a 'thin lens' of known effective power;
(3) the position of the intraocular lens was assumed to be fixed; and
(4) the distance from the surface of the eye (the cornea) to the back surface of the eye (the retina) was a distance that could be measured by clinical methods.

With some variation, the format of these early 'thin lens' intraocular lens power calculation formulas can be described as (Olsen, 2007):

$$P_0 = \frac{n_2}{(Ax-d)} - \frac{1}{\left(\frac{1}{K} - \frac{d}{n_1}\right)}$$

wherein:

K=power of the cornea in dioptres;
d=distance from cornea to the lens plane of the intraocular lens (sometimes referred to as the Anterior Chamber Depth ("ACD") but more correctly referred to as the effective lens plane ("ELP") because the "ACD" strictly speaking is the distance to the anterior surface of the lens and this position does not exist in a 'thin lens' approach);

$n_1$=refractive index for the aqueous humour (the ACD),

Ax=axial length of the eye (distance from cornea surface to retina);

$n_2$=refractive index of medium behind the intraocular lens (the vitreous cavity); and P0=power in dioptres of the intraocular lens needed to produce emmetropia (unaided distance vision) after surgery.

Examples of the 'thin lens' formulae included: Colenbrander (Colenbrander, 1973), Fyodorov (Fyodorov et al., 1975); Binkhorst (Binkhorst, 1975; Binkhorst, 1979); Gernet (Gernet, 1990); Hoffer (Hoffer, 1993a; Hoffer, 2000); Holladay (Holladay et al., 1988).

Behind the simple format of the above-mentioned 'thin lens' intraocular lens power calculation equation there are however several unknowns that should be dealt with in order to work in clinical practice. Some of these unknowns include which refractive index to use, how to accurately calculate the corneal power, the accuracy of the axial length measurements, how to transform distance measurements into optically meaningful distances and how to deal with higher-order aberrations. The most important unknown is however the exact value of 'd' (ELP) which is not a fixed value, as the formula assumes, but subject to a large individual variation. For the formula to work in all cases, the individual ELP therefore needs to be predicted in each case.

Because of the great number of unknowns, all of these available formulas require the use of corrective terms and personalization factors to adjust the formula to real clinical life.

The Empirical Formulae

Soon after the introduction of the early theoretical formulas the clinical experience showed however the accuracy of these formulas to be inferior to the accuracy of the so-called 'empirical formulas'. The latter formulas used a statistical (linear multiple regression) approach to describe a linear relationship between the clinical measurements and the dioptric power of the intraocular lens needed for emmetropia (term used to characterize and eye that does not need spectacles for distance vision).

The most important example of the regression methods is the so-called SRK (Sanders-Retzlaff-Kraff) formulas (Retzlaff, 1980; Sanders et al., 1981; Sanders et al., 1988; Retzlaff et al., 1990; Sanders et al., 1990), which were based on the statistical analysis of a large number of cases with pre-operative measurements of the corneal power (the 'K-reading'), the axial length of the eye as determined by ultrasound (the 'A-scan'), the actual implant power and the observed refraction (the spectacle correction).

The original SRK I formula was a simple linear regression equation (Retzlaff, 1980) as follows:

$$P_0 = A - 0.9K - 2.5Ax$$

wherein:

$P_0$=power of implant for unaided distance vision ('emmetropia');

K=dioptric reading of keratometer (using index 1.3375);

Ax=axial length of the eye as measured by ultrasound; and

A=the 'A-constant' depending on the type of the intraocular lens and the surgical technique.

The idea of the 'A-constant' was that this constant acted a 'black-box' constant capable of absorbing any off-set errors in the system, including differences in intraocular lens type, surgical and measuring techniques and placement in the eye. To overcome systematical off-set errors it was recommended to 'personalize' the 'A-constant' according to the surgeon's own technique.

The success of the original SRK I-formula and the later versions (SRK II, SRK/T) was due to fact that it was based on empirical data and therefore could be made to work without systematical errors in the average case. However, because the formula was based on statistical analysis the predictive value has been shown to be of lower value in unusual eyes like long and short eyes, eye with steep or flat corneas and in eyes with ametropia (Olsen, 1987c; Olsen, 1987b; Olsen et al., 1990b; Olsen et al., 1991). Furthermore, because it was purely dependent on the empirical data including the measuring technique it was not easy to use in different clinical environment with differences (and possible improvements) in surgical or measurement technique, first of all the measurement of axial length.

Furthermore, as can be seen from the mathematics involved in the various 'thin lens' intraocular lens power calculation formulas, the estimation of the ELP is based on the K-reading and the axial length only and embedded in the formula not readily visible to the user.

Early Theoretical Formulae

At the time of the early theoretical formulas very little was known about the actual position of the implant after surgery.

For example the Binkhorst I formula (Binkhorst, 1979) used a fixed value of the ELP to predict the effective position of the implant in each case. Today there is accumulating evidence that the ELP (or the ACD) is not a fixed value but depends on the dimensions of the eye. Among the factors are the pre-operative length of the eye (Ax), the pre-operative anterior chamber depth (ACDpre), the lens thickness and the corneal radius.

Figure 5:
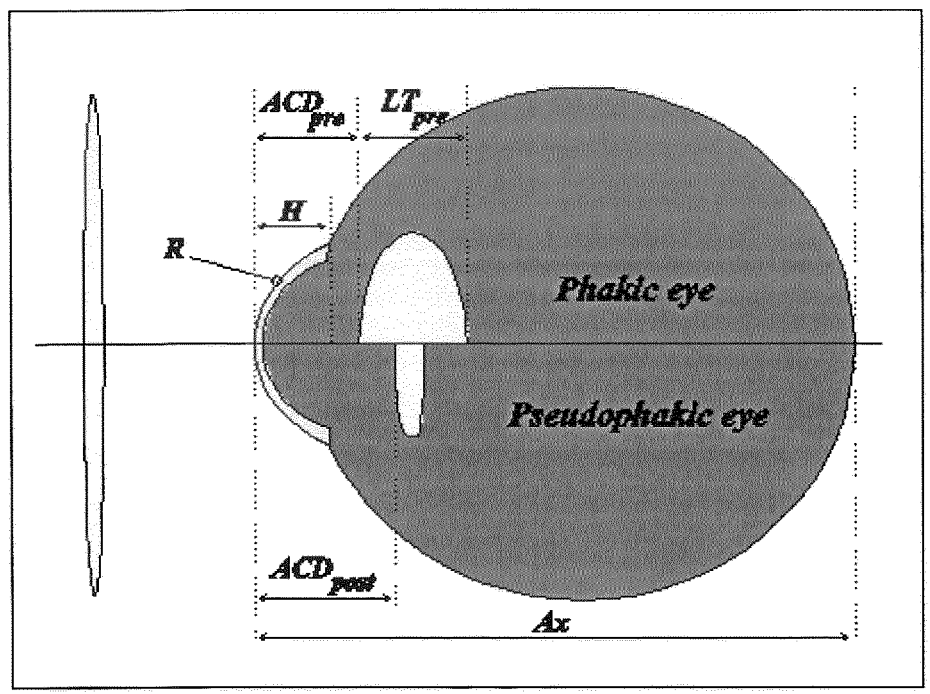

FIG. 5 shows the ocular components of the eye before surgery ('phakic eye'—upper part) and after surgery ('pseudo-phakic eye'—lower part) with important variables used in the prediction of the position of the implant. 'Ax'=axial length, 'ACDpre'=pre-operative ACD, 'LT'=lens thickness, 'CR'=front radius of cornea, 'H'=corneal height, 'ACDpost'=post-operative anterior chamber depth.

Spherical Aberration and the Stiles-Crawford Correction

In the foregoing section, the optics of the eye has been described as a system of combined lenses and it has been assumed that all rays are of equal significance for the image to the picked up by the retina. This need not be the case, however. Due to the existence of the so-called Stiles-Crawford effect (Stiles & Crawford, 1933) the retinal sensitivity is depending on the angle by which the rays hit the retina. The Stiles-Crawford effect predicts the retinal sensitivity to be at a maximum for rays entering the pupil centre and to be of less efficiency for rays entering the pupil edge. The effects follow a mathematical formula:

$$I = I_0 \exp(-0.108 * \gamma^2)$$

wherein:

$\gamma$=distance from the centre of the pupil in mm.

Figure 6:
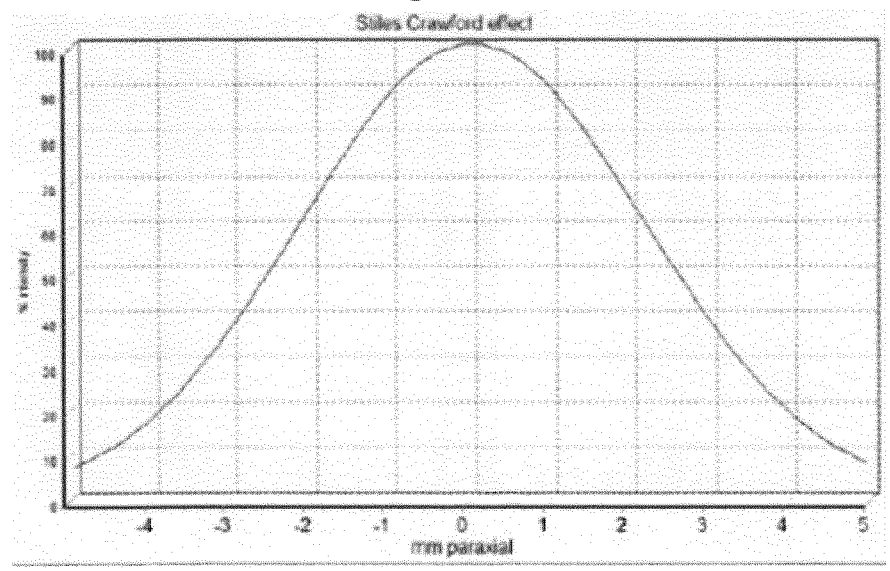

FIG. 6 illustrates the Stiles-Crawford effect showing the retinal sensitivity as a function of the distance from the central axis (x-axis in this figure but y-axis in the ray tracing scheme).

The effect of the Stiles-Crawford effect on the perceived image is that is tends to correct for the effect of spherical aberration when the pupil becomes large (Olsen, 1993). Spherical aberration is a phenomenon of many lenses including the cornea and non-aspheric IOLs, where peripheral rays are refracted more and brought to a focus at a shorter focal length than central rays. The spherical aberration of the human eye is real and accounts for the 'night myopia' that many people experience at mesopic (dim light) conditions where the pupil becomes large.

Spherical aberration is not taken into account when the optics are described according to 'thin lenses' or 'thick lenses' but is readily demonstrated using ray tracing. Another advantage of ray tracing is that the Stiles-Crawford effect can also be accounted for by giving each ray a weight according to the Stiles-Crawford function.

Recent Developments

One of the most important components of any optical formula relating to intraocular lens implants, is the individual prediction of the position of the implant after surgery.

With the exception of the Olsen formula (Olsen, 1987a; Olsen, 1987c; Olsen et al., 1990b; Olsen et al., 1991; Olsen and Corydon, 1993; Olsen and Gimbel, 1993; Olsen, 2004) all the current intraocular lens power calculation formulas methods use virtual models for the position of the intraocular lens after surgery, where the position of the intraocular lens is described not as a physical, measurable distance but rather as a 'effective lens position' (ELP) defined as the distance from the corneal surface to effective lens plane of the intraocular lens, assuming 'thin lens' calculations.

For many years the Olsen formula has been the only formula using a 'thick lens' approach, which means that the cornea and the intraocular lens were treated like a 'thick lens' of finite thickness with exact correction of principal planes. The idea of a 'thick lens' calculation, as first advocated by Olsen (Olsen, 1987a), was that the position of the intraocular lens was defined as a physical measurable distance, which eventually could be verified by clinical methods. Many improvements in intraocular lens power calculations formula deal with improved algorithms for the prediction of the post-operative Anterior Chamber Depth (termed "$ACD_{post}$") (Olsen, 1986b; Holladay et al., 1988; Olsen et al., 1990a; Olsen et al., 1992; Hoffer, 1993b; Olsen et al., 1995; Haigis, 2004; Olsen, 2006).

However, although a 'thick lens' model is superior to a 'thin lens' model with a more realistic representation of the position of the intraocular lens in the eye the 'thick lens' model still assumes spherical surfaces of the optical system. Because neither the cornea nor the intraocular lens are necessarily spherical, a better model might be based on exact ray tracing, which can be made to work on any surface type.

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIG. 1—Schematic diagram of the human eye, in which the various anatomical parts and structures are indicated.

FIG. 2—Model of an eye showing the refraction of light and image formation. The refraction of light through the eye takes place in the cornea (1) and the lens (2) in order to focus light at the retina (3) at the back of the eye. If there is an imbalance between any of the ocular components, the eye will need spectacle-correction to see clearly.

FIG. 3—An example of an optical scan of a normal, phakic eye performed by the Haag-Streit Lenstar biometer. The position of the normal, crystalline lens is indicated by pointing hands.

FIG. 4—An example of a post-operative scan of the same eye shown in FIG. 3 one week after surgery with an IOL in place. The position of the IOL is indicated by pointing hands FIG. 5—Illustration of the ocular components of the eye before and after surgery.

FIG. 6—Illustration of the Stiles-Crawford effect.

Figure 7:
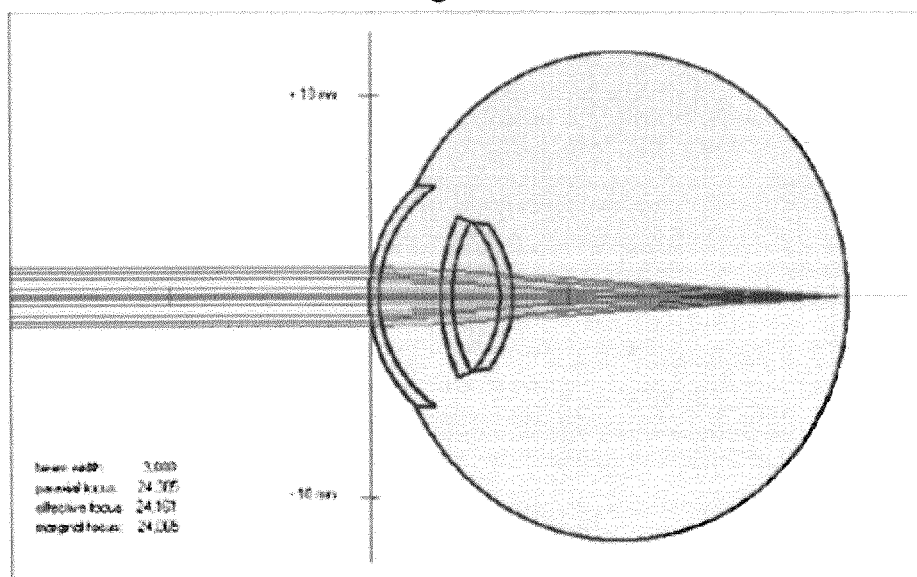

FIG. 7—An example of a ray trace of Gullstrand exact schematic eye.

Figure 8:
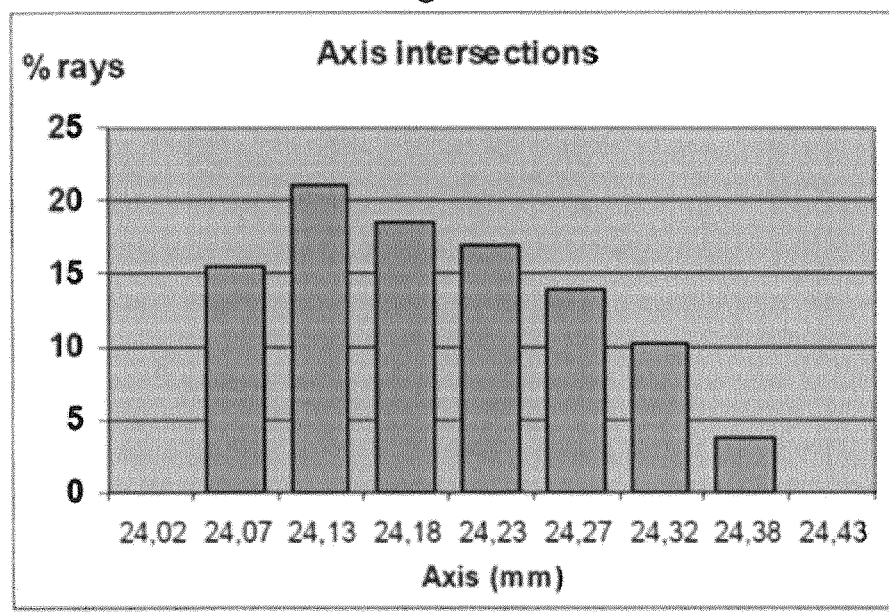

FIG. 8—Distribution of the x-axis ray intersections (number of rays=1000) for the Gullstrand eye assuming a pupil of 3 mm. It is noted that all rays are brought to a focus behind the retina at 24.0 mm. The eye is therefore slightly longsighted (hyperopic).

Figure 9:
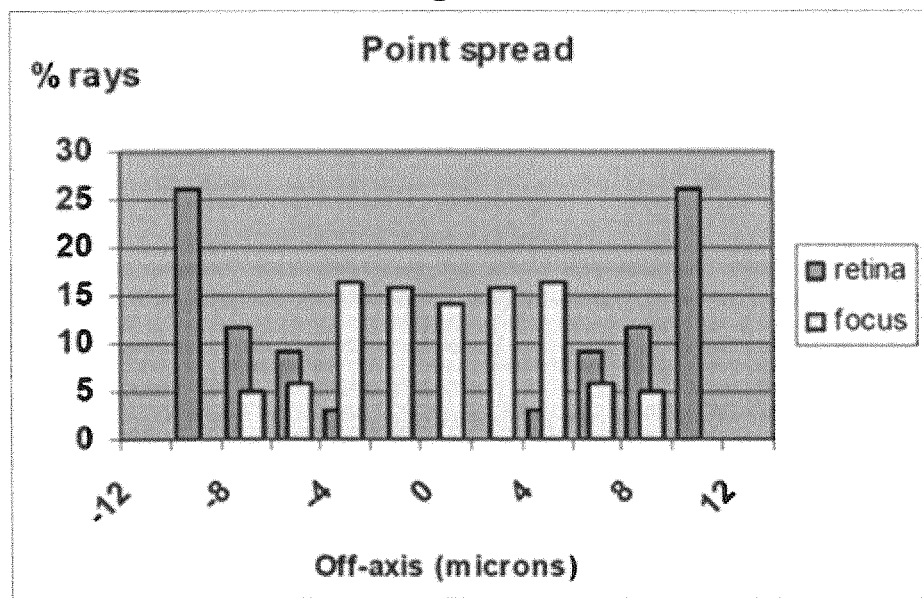

FIG. 9—Illustration of the point spread function of the Gullstrand eye at the retina (dark columns) and at the best focus 0.194 mm behind the retina (light columns).

Figure 10:
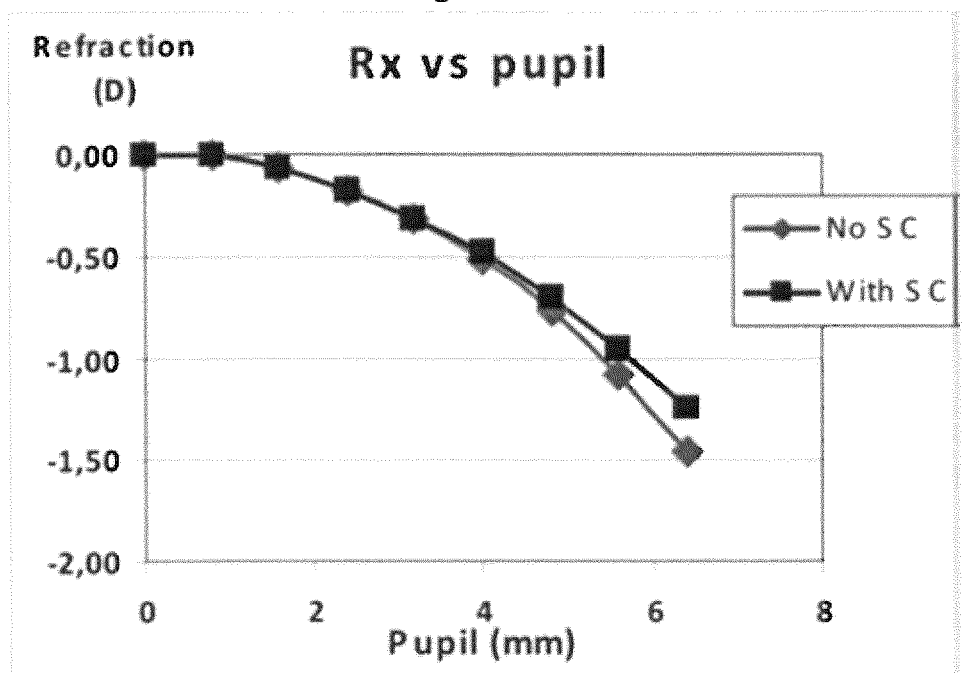
Figure 11:
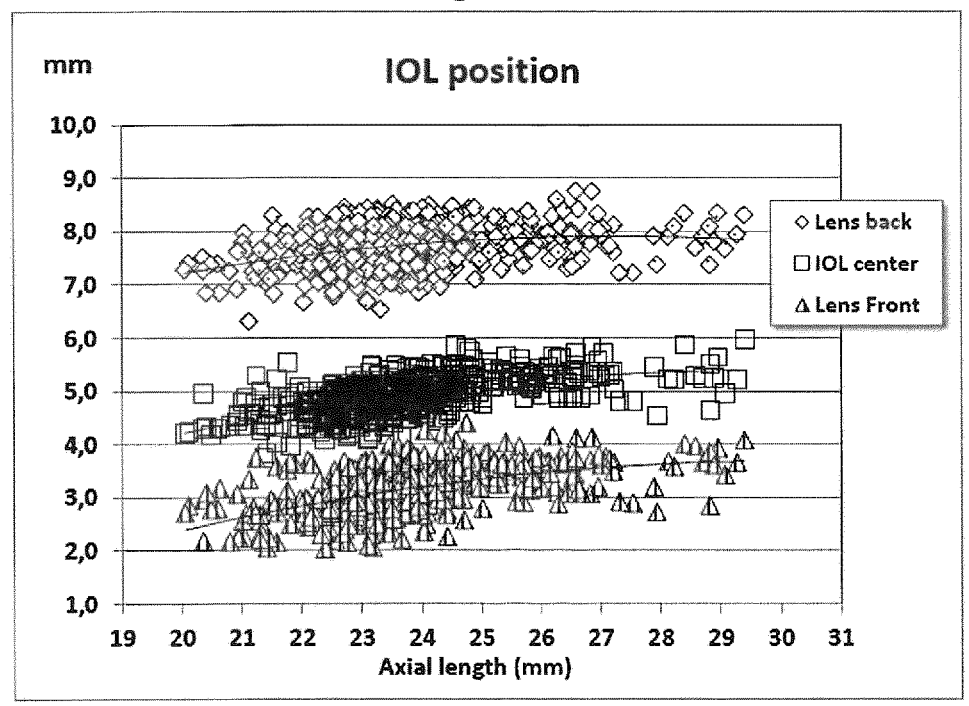

FIG. 10—Illustration of the effect of pupil size on the refraction predicted for a normal eye of average dimension with a spherical intraocular lens implant FIG. 11—The measured intraocular lens position (squares) relative to position of anterior (triangles) and posterior capsule (diamonds) plotted against the axial length (x-axis).

Figure 12:
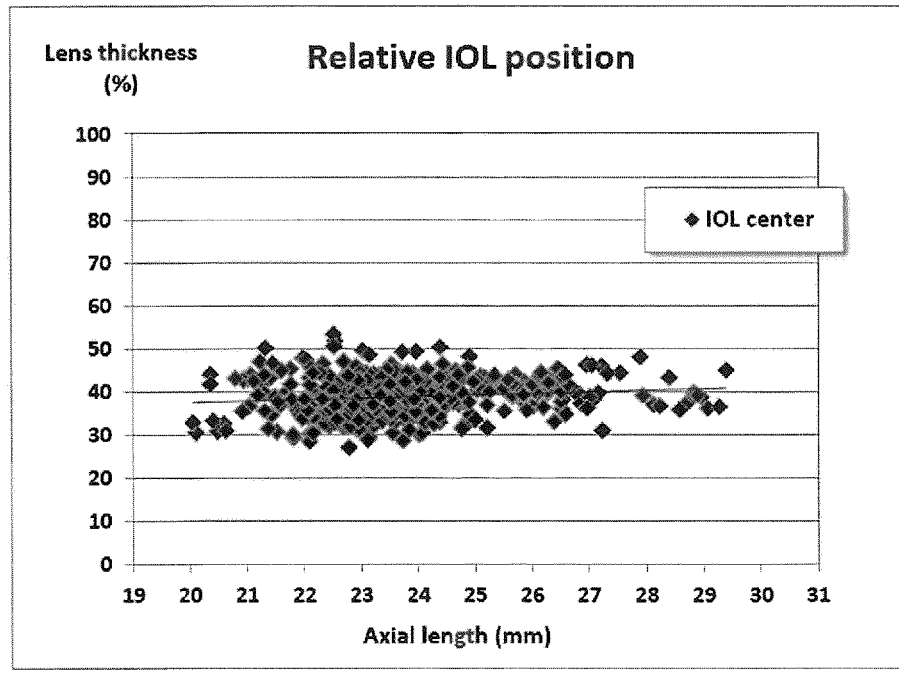

FIG. 12—The intraocular lens position expressed as fraction of lens thickness plotted against the axial length.

Figure 13:
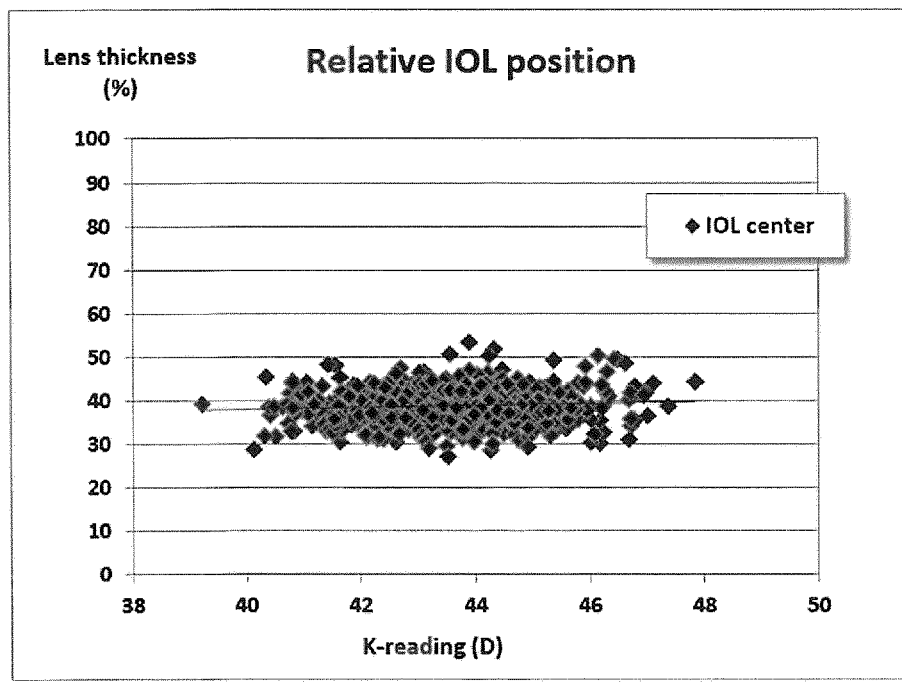

FIG. 13—The intraocular lens position expressed as fraction of lens thickness plotted against the corneal power by keratometry.

Figure 14:
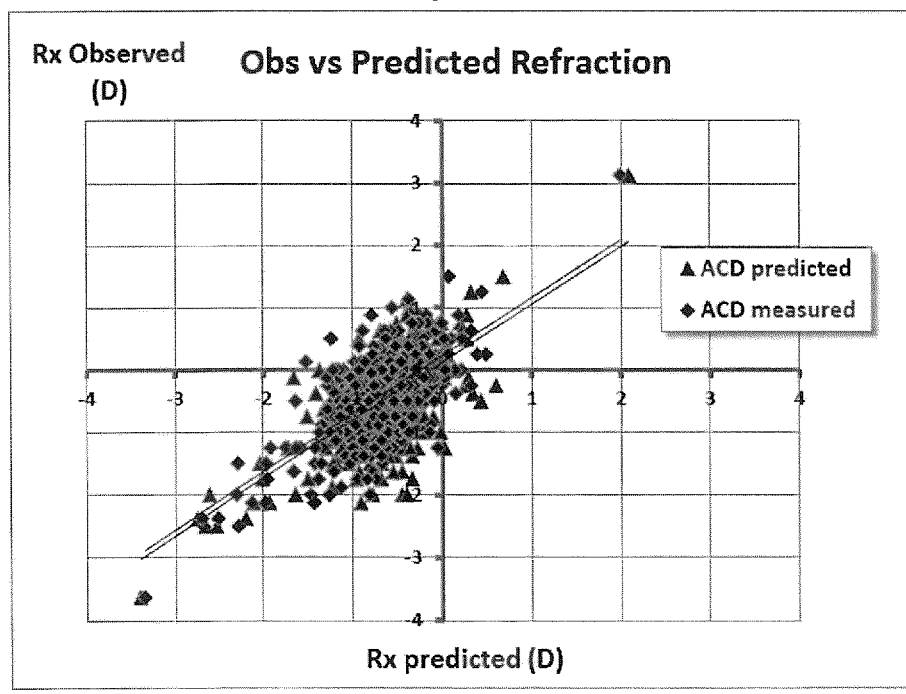

FIG. 14—The observed refraction plotted against the expected (predicted) refraction for two methods using 'ACD measured' and 'ACD predicted' values for the position of the intraocular lens implant.

Figure 15:
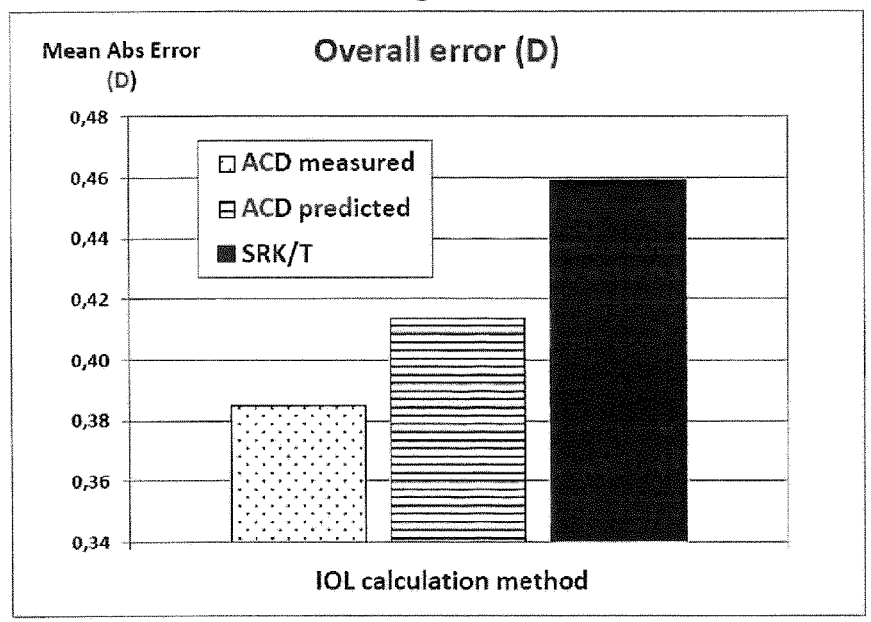

FIG. 15—The mean absolute error of three intraocular lens power calculation methods for the calculation of the expected refraction.

Figure 16:
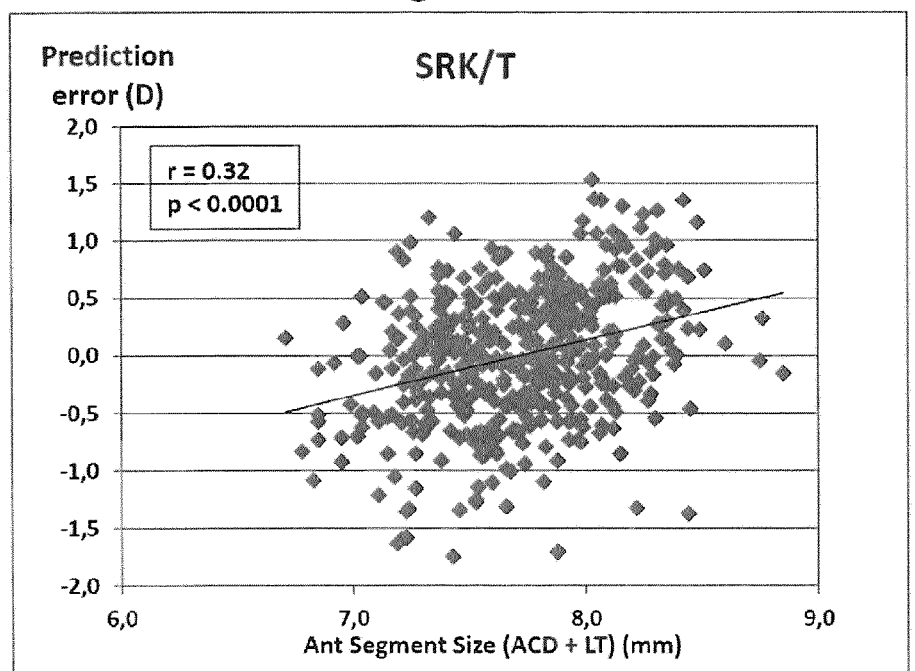

FIG. 16—Prediction error (observed refraction minus expected refraction) according to the SRK/T formula plotted against the anterior segment size (anterior chamber depth+lens thickness=position of posterior surface of the crystalline lens). A significant bias was observed (r=0.32, p<0.0001).

Figure 17:
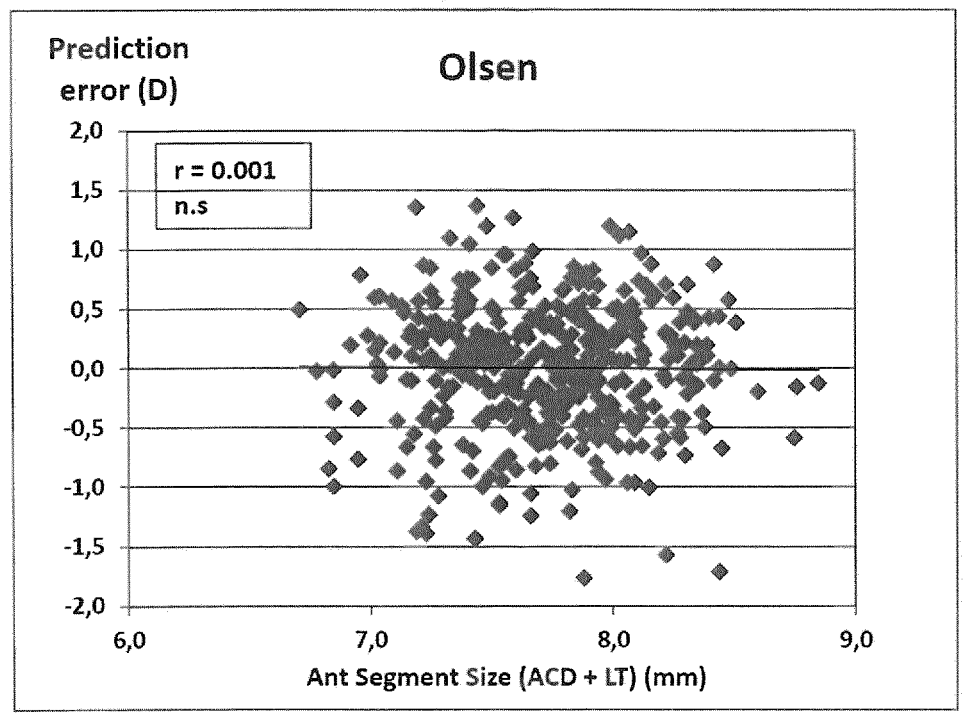

FIG. 17—Prediction error (observed refraction minus expected refraction) according to the formula of the present invention plotted against the anterior segment size (anterior chamber depth+lens thickness=position of posterior surface of the crystalline lens). A non-significant correlation was observed indicating no bias (r=0.001, p>0.5).

Figure 18:
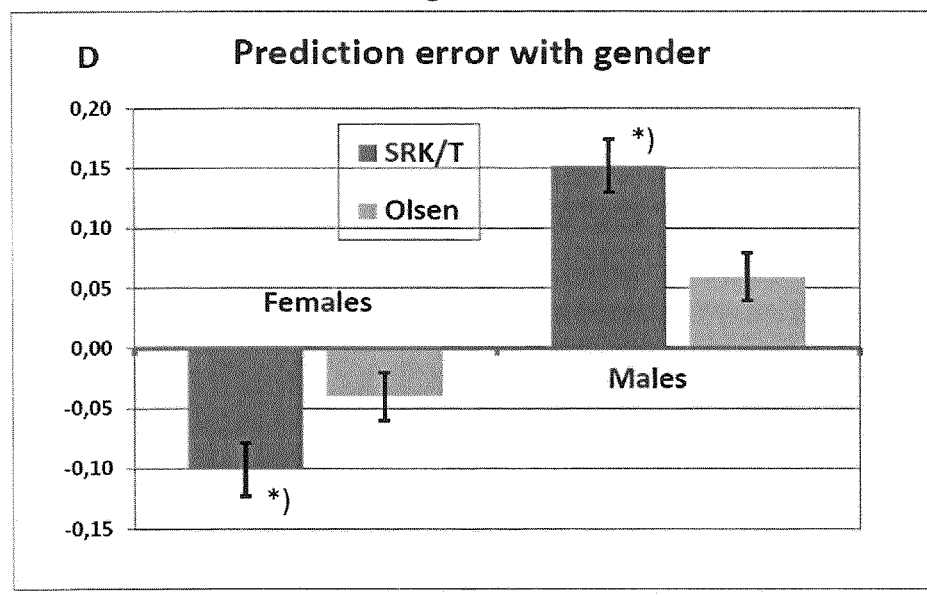

FIG. 18—Mean prediction error (observed refraction minus expected refraction) subdivided into females (n=274) and males (n=181) according to the SRK/T and the formula of the present invention, respectively. The mean prediction error was kept zero for the total group (n=455) including both females and males by IOL constant optimization. A significant bias with gender is seen with the SRK/T method but not with the present method (p<0.05). Bars indicate standard error (SE).

Figure 19:
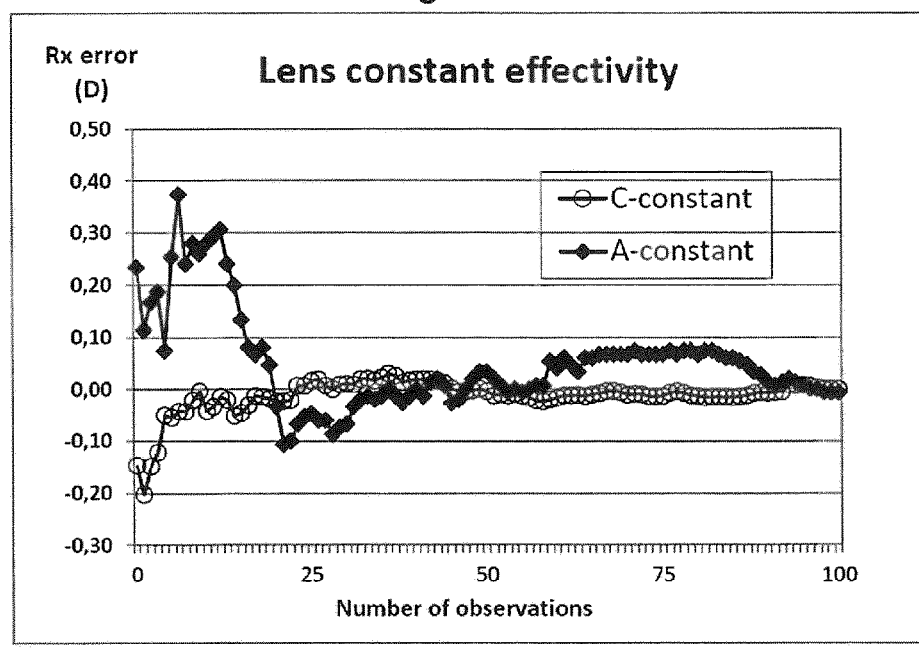

FIG. 19—Comparison of the C-constant with the A-constant

EXAMPLES

Example 1

Ray Tracing Analysis of Gullstrand Eye

The exact schematic eye of Gullstrand (Gullstrand, 1909, Gullstrand, 1924) was used as an example of the ray tracing analysis. For many years the exact schematic eye of Gullstrand has been used to simulate the optical properties of the human eye. Apart from the object plane and the image plane the structure of the schematic eye is a six surface model as shown in Table 1.

TABLE 1

Surfaces of the exact schematic eye of Gullstrand. Each surface is given number from left to right, a name, an axis location (x-Position), a radius of curvature (positive means anterior convex and negative means anterior concave), a conic coefficient (zero for this eye model) and a refractive index.

| Surface | Name | x-Position | Radius | Conic | index |
|---|---|---|---|---|---|
| 0 | Object | −30 | 10000 | 0 | 1 |
| 1 | Cornea front | 0 | 7.7 | 0 | 1.38 |
| 2 | Cornea back | 0.5 | 6.8 | 0 | 1.34 |
| 3 | Lens front | 3.6 | 10 | 0 | 1.39 |
| 4 | Nucleus front | 4.15 | 7.91 | 0 | 1.41 |
| 5 | Nucleus back | 6.57 | −5.76 | 0 | 1.39 |
| 6 | Lens back | 7.2 | −6 | 0 | 1.34 |
| 7 | Retina (image) | 24 | −13 | 0 | 0 |

In the Gullstrand eye the axial length of the eye is assumed to be 24.00 mm, which is the location of the retina where the image is perceived. An example of a ray trace of this eye, the structure of which is listed in Table 1, is shown in FIG. 7 for an entrance beam width of 3 mm with a limited number of incoming parallel rays. Rays are assumed to origin at infinity and being refracted at each surface according to Snell's law of refraction until they hit the posterior surface of the eye (the retina).

When using a sufficient number of rays (>1000 or more) the distribution of the ray intersections on the x-axis can be studied to give an estimate of the effective focus along the visual axis. Likewise the distribution of the ray intersections with the retina (which can be regarded as a slightly curved y-axis) can also be studied. The latter distribution is known in optical terms as the point-spread function ('PSF'), which is a measure of the image quality. As a measure of the spread it is common practice to calculate the root-mean-square ('RMS') of the distances from the axial focus.

In FIG. 8 is shown the distribution of the x-axis ray intersections (number of rays=1000) for the Gullstrand eye assuming a pupil of 3 mm. It is noted that all rays are brought to a focus behind the retina at 24.0 mm. The eye is therefore slightly longsighted (hyperopic).

The analysis of the point-spread-function in the y-direction was provided at two planes: 1) at the retina and 2) at the best focus, which was found by computer iteration to locate about 0.194 mm behind the retina. FIG. 9 illustrates the point spread function of the Gullstrand eye at the retina (dark columns) and at the best focus 0.194 mm behind the retina (light columns). The corresponding RMS was found to be 0.256 and 0.109 at the retina and at the best focus, respectively.

In conclusion, this experiment has shown that the quality of the image giving the least blur would be enhanced if the axial length of the eye had been 0.194 mm longer or, alternatively, if a small spectacle correction with a power of about +0.5 D (equivalent value of shift in axial length) had been placed in front the eye.

Example 2

Ray Tracing Analysis of Eye with IOL Implant

The following ray tracing example shows an eye of average dimension with a spherical IOL implanted to give good uncorrected vision at a negligible pupil size. The effective refraction was plotted against the diameter of the pupil with and without correction for the Stiles-Crawford effect.

FIG. 10 illustrates the effect of pupil size on the refraction predicted for a normal eye of average dimension with a spherical IOL implant. As the pupil widens, the eye becomes myopic as a result of spherical aberration. The effect is compensated for by the Stiles-Crawford effect ('SC').

Two observations can be drawn from FIG. 10:
(1) The effective refraction is dependent on the pupil size also within the normal range (less than 3-4 mm), and
(2) The Stiles-Crawford effect compensates for the spherical aberration at larger pupil sizes.

IOL Data

The assumed physical characteristics of the IOL (thickness, refractive index, front and back curvature were obtained from the 'cutting chart' provided by Alcon). An example of the cutting chart is given in Table 2:

TABLE 2

'Cutting' chart provided from Alcon Laboratories showing the radii of the anterior and posterior surface of the IOL according to power. The refractive index is 1.5542 (Wavelength 550 nm) and the thickness is 0.8 mm for a normal power of about 23.0 D. (Data provided by Alcon Laboratories).
SA60AT & SN60AT

| Diopter Range | Anterior Radii | Posterior Radii |
|---|---|---|
| 6.0-9.5 D | 35-81 mm | 75.0 mm |
| 10.0-15.5 D | 22-52 mm | 37.7 mm |
| 16.0-25.0 D | 13.4-29.9 mm | 25.1 mm |
| 25.5-30.0 D | 12.6-16.9 mm | 17.48 mm |
| 31.0-40.0 D | 6.9-9.8 mm | 25.1 mm |

By ANSI definition, the power of an IOL can be calculated as the 'thick lens' paraxial power:

$$D_{12} = D_1 - (T/n) D_1 D_2$$

wherein:
$D_{12}$=total dioptric power of the lens;
$D_1$=dioptric power of front surface;
$D_2$=dioptric power of back surface;
T=thickness of lens (in meters); and
n=refractive index.
$D_1$ and $D_2$ can be found as:

$$D_1 = (n - 1.336)/r_1$$

and $$D2 = (1.336 - n)/r_2$$

wherein:
$r_1$=radius of curvature of front surface (m);
$r_2$=radius of curvature of back surface (with sign convention); and
n=refractive index of the lens.

In this way the exact curvatures of the IOL can be found from the labelled power according to the scheme in Table 2

Example 3

Clinical Data: Identifying the Constant, C

Summary
As discussed in the accompanying description, the invention is based on the inventor's discovery that the post-operative position of an intraocular lens is related to certain defined anatomical and physical characteristics of the preoperative eye—in particular, the position and the thickness of the normal, biological, crystalline lens in the pre-operative eye of the patient. Thus, in light of the inventor's discovery, the measurement of certain physical parameters in the eye of a patient prior to surgery (in particular, the crystalline lens position and thickness) can be used to predict the specific post-operative position that an implanted intraocular lens will occupy in the eye of that patient.

That discovery arose from the studies discussed below. In brief, those studies involved the following steps:

(1) the statistical analysis of a plurality of patients having lens surgery;

(2) measuring the following preoperative parameters of the eye of the patient: the corneal radius, the axial length, the preoperative anterior chamber depth and the crystalline lens thickness;

(3) measuring the following postoperative parameters of the eye: the final refraction (spectacle correction) and the position of the IOL;

(4) demonstrating that the measured position of the IOL can be used in the optical model of the pseudophakic (IOL) eye;

(5) generating a surprisingly simple formula predicting the post-operative position of the IOL based on a constant fraction of the biological crystalline lens thickness, depending on the IOL model and surgical technique.

Materials and Methods

A total of 590 cases (250 males and 340 females in the age range 20-94 years, mean 70.1 years, were included in the study. They comprised a consecutive series of patients referred for cataract or clear-lens surgery at the University Eye Clinic, Aarhus Hospital with uncomplicated implantation of an IOL of similar design (Alcon Acrysof SA60AT) into the capsular bag.

Before surgery the anterior corneal radius was measured in two meridians by an auto-kerato-refracto-meter (ARK700; Nidek, Hiroishi, Japan) and the two readings averaged, which is the common procedure when dealing with spherical equivalents. The axial length was measured using optical interferometry (Zeiss IOLMaster (Zeiss Meditec, Jena, Germany). The Anterior Chamber Depth (termed "ACDpre") and the crystalline lens thickness (termed "LT") of the pre-operative eye of the patients were measured using optical interferometry (Haag-Streit LS900 Lenstar).

Exclusion criteria were eyes with complications during surgery, IOL implantation outside the capsular bag, dislocated lenses, previous anterior (i.e. LASIK), or posterior segment surgery, negative IOL power and pre-operative or post-operative astigmatism larger than 4D. For the present study, only cases with a post-operative best corrected visual acuity of 20/50 or more were included in order to have a reliable estimate of the final spectacle correction (the refraction).

The post-operative follow-up time was set from 1 week to 3 months. At that time the visual acuity and the refraction were recorded. The post-operative Anterior Chamber Depth (termed "ACDpost") was measured using optical interferometry (Haag-Streit LS900 Lenstar).

A summary of the clinical data is shown in Table 3.

TABLE 3

Clinical data of 590 cases with a known IOL implant. The axial length, the pre-operative ACD and the crystalline lens thickness were measured by laser interferometry. Mean values (+SD, standard deviation) and ranges are shown

| Data | Age (years) | Keratometry (D) | Axial Length (mm) | Preop ACD (mm) | Preop LT (mm) | IOL power (D) |
|---|---|---|---|---|---|---|
| Mean | 70.1 | 43.6 | 23.70 | 3.13 | 4.59 | 20.81 |
| (+SD) | (+13.1) | (+1.45) | (+1.52) | (+0.42) | (+0.47) | (+4.24) |
| Range | 20-94 | 39.2-47.8 | 20.10-29.39 | 2.01-4.40 | 2.97-5.93 | 4.0-34.0 |

Results

Measurement of the Post-operative Anterior Chamber Depth

The mean position of the (centre of the) IOL after surgery was 4.90 mm+0.35 (+SD) (range 3.30-5.78 mm). This was defined as the measured anterior chamber depth+half of the known thickness of the IOL. When plotted against the axial length and the pre-operative position of the biological crystalline lens it can be seen, that the position of the IOL was a constant fraction of the thickness of the crystalline lens ('bag size') (FIG. 11).

Expressed as the fraction of the crystalline lens thickness the IOL position showed small positive correlation with the axial length, which was barely significant (r=0.13, p<0.01, FIG. 12).

As shown in FIG. 13, the IOL position showed a non-significant correlation with the keratometry (r=0.04, p>0.2).

The very weak or non-significant correlation with axial length and keratometry is an important observation, as this means the prediction of the IOL position can be made independently from both the K-reading and the axial length, contrary to what is assumed in all existing formulas today.

Formula to Predict the Position of the IOL

Based on the observation that the position of the IOL is a constant fraction of the crystalline lens thickness the following formula could be established predicting the IOL position in the individual case:

$$IOL_{predicted} = ACD_{pre} + C*LT$$

wherein:

$IOL_{predicted}$ is the expected post-operative (central) position of the IOL;

$ACD_{pre}$ is the pre-operative anterior chamber depth;

LT is the crystalline lens thickness;

C is a numerical constant (C) related to the IOL type (=38.7% in current dataset).

Results of IOL Power Calculation

To verify the hypothesis that this method can be used in the calculation of the IOL power in the individual case several experiments were performed:

Experiment 1: Using the observed (measured) ACD, the expected post-operative refraction was calculated using ray tracing formula as described in the preceding sections. This experiment is to be regarded as the experiment showing the ultimate accuracy resulting from a perfect method showing no error predicting the IOL position.

Experiment 2: Using the new ACD formula (i.e. $IOL_{predicted} = ACD_{pre} + C \times LT$), the expected post-operative refraction was calculated using the ray tracing formula as described in the preceding sections.

Experiment 3: As a reference, the IOL power was calculated using the popular SRK/T method which is one of the most popular IOL power calculation methods used today.

In all these experiments, the predictions were analysed for mean numerical error, standard deviation and range of error. In case of the SRK/T formula, the predictions were optimized as recommended by the authors so that the A-constant used was accurate in the average case. As is the case when evaluating formula accuracy in the field of clinical IOL power calculation, all methods were optimized for small off-set errors adjusting the numerical mean error to zero. In doing this, it is possible to evaluate formula performance by comparing the standard deviation of the error, or alternatively—as is usually the case in the field of IOL power calculation studies—by comparing the absolute error for each method.

In Table 4 is shown the results of the three experiments. As can be seen the lowest error (lowest standard deviation, lowest mean absolute error, smallest range of errors and the highest percentage of cases within +1.0 D) was found with the method using the observed (measured) ACD post-operatively.

TABLE 4

Error of 3 methods to calculate the refractive outcome after IOL implantation. Method 'ACD measured' is based on the optical model of the pseudophakic eye using ray tracing and the actual (measured) position of the IOL. Method 'ACD predicted' is based on the same optical model but using a predicted (calculated) position of the IOL according to Eq 1. Method 'SRK/T' is based on the current Sanders-Retzlaff-Kraff ('theoretic') formula which is one of the most widely used formula for IOL power calculation today. The error is stated as the difference between the observed and expected refraction (spherical equivalent) in the spectacle plane expressed and Dioptres (observed minus expected).

| IOL calc method | ACD measured | ACD predicted | SRK/T |
|---|---|---|---|
| Mean error (D) | 0.00 | 0.00 | 0.00 |
| SD (D) | 0.494 | 0.536 | 0.580 |
| Range (D) | −1.48-+1.45 | −1.55-+1.58 | −1.75-+1.53 |
| Mean abs error | 0.385 | 0.413 | 0.459 |
| Error <+0.5 (%) | 70.4 | 67.1 | 60.7 |
| Error <+1.0 (%) | 95.6 | 93.2 | 91.8 |
| Error <+1.5 (%) | 100 | 99.1 | 98.7 |
| Error >=+1.5 (%) | 0 | 0.9 | 1.3 |

Comparison of Experiments 1 and 2

These two experiments were in close agreement, at can be seen in FIG. 14 showing the observed refraction plotted against the expected (predicted) refraction for the two methods. Correlation coefficients were 0.88 and 0.82 for experiment 1 and 2 respectively ($p<0.001$).

The Overall Error of the 3 Experiments

In FIG. 15 is the graphic comparison of the mean absolute error of the 3 methods. There was a statistically significant difference in accuracy between all 3 methods ($p<0.05$).

Further Results Showing Improvement Over Current Methods

Bias with Anterior Segment Size

As described in the foregoing sections, one of the advantages of the present invention is that it uses the pre-operative anterior chamber depth and the lens thickness as predictors for the position of the IOL. This is in contrast to other IOL power calculation formulas which use the K-reading and the axial length for all calculations including both the optical calculations and the prediction of the IOL position.

The fact that the IOL position is depending on the preoperative anterior chamber depth and the lens thickness as shown in the present invention leads to the hypothesis that other IOL power calculation formulas like the most popular SRK/T formula may show a bias with the anterior segment size (Anterior segment size=anterior chamber depth+lens thickness).

As shown in FIG. 16, this was actually the case in a series of 455 cases when the prediction error of the SRK/T formula was plotted against the pre-operative anterior segment size ($r=0.32$, $p<0.001$). The bias, which is undesirable, was not seen with the present approach (FIG. 17).

Bias with Gender

Another improvement is found with gender bias. It is well known from population studies that female and male eyes differ slightly in many ways. Examples are the corneal radius, the anterior chamber depth and the axial length which are smaller in females than in males. Also the average IOL position differs slightly, as can be demonstrated in a sufficiently large sample (unpublished observations by the author). This would pose a problem if one would like to use the same IOL constants for both females and males.

However, due to concept of the 'C' constant in the present invention which predicts the IOL position relative to the individual anatomy of the crystalline lens, it may be hypothesized that this method is not as prone to gender bias as the A-constant method of the SRK method which is based on the average IOL power valid for a case mix of both females and males.

As shown in FIG. 18 this was actually found to be the case when the total series was subdivided according to gender. The total series comprised 455 individuals (274 females and 181 males) where the refractive predictions have been corrected for average off-set errors by optimizing the IOL constant for the group as a whole. With the SRK/T formula, an average prediction error of −0.10 D and +0.15 D was found in the females and males, respectively, which was significantly different from zero ($p<0.05$). With the present method the average prediction error was found to be −0.04 D and +0.05 D in females and males, respectively, which was not significantly different from zero ($p>0.05$). The present method therefore shows no bias with gender.

Conclusions

1. The current invention predicts the position of the IOL implanted in the capsular bag according to accurate measurements of the position and thickness of the natural crystalline lens
2. The formula predicts the centre of the IOL to be a constant fraction 'C' of the crystalline lens thickness ('bag size'), depending on the IOL style and the surgical technique. Once the average position of the IOL has been determined in a sufficient number of cases, the 'C' value can be derived for the particular IOL.
3. The prediction of the IOL position is made independently of the measurements of the corneal power ('K-reading') and the axial length, which traditionally have been used in other formulas.
4. The optical model of the eye used in the present approach can utilize the information from measurements of the IOL position (as well as predicted values) to make accurate predictions
5. The resulting accuracy of the IOL power calculation is higher than with current methods like the SRK/T formula and the predictions show no bias with axial length, anterior segment size and gender.
6. Because the method relates specifically to the anatomy of the lens to be operated on, the method should work in any type of eye, including eyes that have undergone changes of the corneal anatomy, like post-refractive surgery (LASIK, LASEK, PRK, RK etc) patients having had corneal surgery for refractive errors.

Example 4

Variation in the C Constant

The position of the IOL within post-operative eye (and hence the numerical constant, C) may be influenced by the geometry of the IOL that is implanted, particularly because the diameter, shape and mechanical properties of the haptics may influence how the IOL will be pushed forward or backward as a result of the gradual contraction of the capsule after surgery.

However, as discussed below, the variation in the C value obtained using two different IOL types is surprisingly small.

Table 5 shows data obtained from two different IOLs which have different geometry and design. As can be seen the C-constant differs by only 0.06 between the two IOLs, corresponding to only 0.29 mm assuming average eye data.

| IOL | No. of individuals | Mean C value | SD | Min C value | Max C value |
|---|---|---|---|---|---|
| Alcon SA60AT | 100 | 0.38 | 0.04 | 0.31 | 0.58 |
| AMO ZCB00 | 24 | 0.44 | 0.05 | 0.33 | 0.57 |

Example 5

Comparison of the C Constant with the A-constant

The method of the present invention is performed using the numerical constant, C, which defines the relationship between the post-operative position of the IOL in the eye of two or more eye-operated individuals, relative to the thickness of the crystalline lens in the pre-operative eye of the two or more eye-operated individuals.

The constant C can be determined using data obtained from a relatively small number of eye-operated patients, rendering it advantageous over previous methods (such as those using the A-constant) which require data from larger data sets.

The minimum number of eye-operated patients needed can be derived from the statistical analysis of data that has already been obtained using the present invention. For example, a typical finding is a mean value of C=39% with a standard deviation of only 4%. The small standard deviation means that very few cases are required to obtain a statistically-meaningful estimate of the constant, C.

This is in contrast to (all) other formulas using "fudged" constants (i.e. the A-constant) derived from the observed final spectacle correction.

FIG. 16 provides a numerical example illustrating the favourable benefit of the C-constant as compared to the A-constant in the analysis of aggregated data. FIG. 16 has been constructed from a random sample of clinical data by calculating the observed mean value of the new C-constant as compared to the old A-constant, and transforming the deviation from the final mean into error in the spectacle correction (Rx). As can be seen, the C-constant rapidly reaches a reasonable accuracy within 0.1 D whereas the curve for the A-constant takes at least 25 cases to do so.

FIG. 19 provides a numerical example illustrating the favourable benefit of the C-constant as compared to the A-constant in the analysis of aggregated data. FIG. 16 has been constructed from a random sample of clinical data by calculating the observed mean value of the new C-constant as compared to the old A-constant, and transforming the deviation from the final mean into error in the spectacle correction (Rx). As can be seen, the C-constant rapidly reaches a reasonable accuracy (within 0.1 D) within the first 25 cases whereas the curve for the A-constant takes at least 50 to 100 cases to stabilize.

REFERENCES

Baker T Y. Ray-tracing trough non-spherical surfaces. Proc Physical Soc (UK) 1943; (24): 361-364.

Binkhorst R D. The optical design of intraocular lens implants. Ophthalmic Surg 1975; (6): 17-31.

Binkhorst R D. Intraocular lens power calculation. Int Ophthalmol Clin 1979; (19): 237-252.

Colenbrander M C. Calculation of the power of an iris clip lens for distant vision. Br J Ophthalmol 1973; (57): 735-740.

Connors R, III, Boseman P, III, Olson R J. Accuracy and reproducibility of biometry using partial coherence interferometry. J Cataract Refract Surg 2002; (28): 235-238.

Drexler W, Findl O, Menapace R, Rainer G, Vass C, Hitzenberger C K, Fercher A F. Partial coherence interferometry: a novel approach to biometry in cataract surgery. Am J Ophthalmol 1998; (126): 524-534.

Dubbelman M, Sicam V A, van der Heijde G L. The shape of the anterior and posterior surface of the aging human cornea. Vision Res 2006; (46): 993-1001.

Dubbelman M, Weeber H A, van der Heijde R G, Volker-Dieben H J. Radius and asphericity of the posterior corneal surface determined by corrected Scheimpflug photography. Acta Ophthalmol Scand 2002; (80): 379-383.

Dunne M C, Royston J M, Barnes D A. Normal variations of the posterior corneal surface. Acta Ophthalmol (Copenh) 1992; (70): 255-261.

Findl O, Kriechbaum K, Sacu S, Kiss B, Polak K, Nepp J, Schild G, Rainer G, Maca S, Petternel V, Lackner B, Drexler W. Influence of operator experience on the performance of ultrasound biometry compared to optical biometry before cataract surgery. J Cataract Refract Surg 2003; (29): 1950-1955.

Fyodorov S N, Galin M A, Linksz A. Calculation of the optical power of intraocular lenses. Invest Ophthalmol 1975; (14): 625-628.

Gernet H. [Intraocular lens planning. Geometric-optical and Sanders-Retzlaff-Kraff I and II formulas]. Ophtalmologie 1990; (4): 96-101.

Gullstrand A. Die Dioptrik des Auges. In: Handbuch der physiologischen Optik. (Ed. Helmholz H). Hamburg: L Voss, 1909; 3: 41-375.

Gullstrand A. The dioptrics of the eye. In: Helmholtz's Treatise on Physiological Optics. (Ed. Southall J P C). Optical Society of America, 1924; 351-352.

Haigis W. Pseudophakic correction factors for optical biometry. Graefes Arch Clin Exp Ophthalmol 2001; (239): 589-598.

Haigis W. The Haigis formula. In: Intraocular lens power calculations. (Ed. Shammas H J). Slack Inc, 2004; 5-57.

Haigis W, Lege B, Miller N, Schneider B. Comparison of immersion ultrasound biometry and partial coherence interferometry for intraocular lens calculation according to Haigis. Graefes Arch Clin Exp Ophthalmol 2000; (238): 765-773.

Hoffer K J. The Hoffer Q formula: a comparison of theoretic and regression formulas. J Cataract Refract Surg 1993b; (19): 700-712.

Hoffer K J. The Hoffer Q formula: a comparison of theoretic and regression formulas. J Cataract Refract Surg 1993a; (19): 700-712.

Hoffer K J. Clinical results using the Holladay 2 intraocular lens power formula. J Cataract Refract Surg 2000; (26): 1233-1237.

Holladay J T, Prager T C, Chandler T Y, Musgrove K H, Lewis J W, Ruiz R S. A three-part system for refining intraocular lens power calculations. J Cataract Refract Surg 1988; (14): 17-24.

Jansson F, Kock E. Determination of the velocity of ultrasound in the human lens and vitreous. Acta Ophthalmol (Copenh) 1962; (40): 420-433.

Kiss B, Findl O, Menapace R, Wirtitsch M, Petternel V, Drexler W, Rainer G, Georgopoulos M, Hitzenberger C K, Fercher A F. Refractive outcome of cataract surgery using partial coherence interferometry and ultrasound biometry: clinical feasibility study of a commercial prototype II. J Cataract Refract Surg 2002; (28): 230-234.

Olsen T. On the calculation of power from curvature of the cornea. Br J Ophthalmol 1986a; (70): 152-154.

Olsen T. Prediction of intraocular lens position after cataract extraction. J Cataract Refract Surg 1986b; (12): 376-379.

Olsen T. Theoretical approach to intraocular lens calculation using Gaussian optics. J Cataract Refract Surg 1987a; (13): 141-145.

Olsen T. Theoretical vs empirical prediction of aphakic refraction. Arch Ophthalmol 1987b; (105): 1042-1045.

Olsen T. Theoretical, computer-assisted prediction versus SRK prediction of post-operative refraction after intraocular lens implantation. J Cataract Refract Surg 1987c; (13): 146-150.

Olsen T. On the Stiles-Crawford effect and ocular imagery. Acta Ophthalmol (Copenh) 1993; (71): 85-88.

Olsen T. The Olsen formula. In: Intraocular lens calculations. (Ed. Shammas H J). Thorofare, N J: Slack Inc, 2004; 27-40.

Olsen T. Prediction of the effective post-operative (intraocular lens) anterior chamber depth. J Cataract Refract Surg 2006; (32): 419-424.

Olsen T. Calculation of intraocular lens power: a review. Acta Ophthalmol Scand 2007; (85): 472-485.

Olsen T, Corydon L. We don't need fudge factors in IOL power calculation. Eur J Implant Refract Surg 1993; (5): 51-54.

Olsen T, Corydon L, Gimbel H. Intraocular lens power calculation with an improved anterior chamber depth prediction algorithm. J Cataract Refract Surg 1995; (21): 313-319.

Olsen T, Funding M. Ray-tracing analysis of intraocular lens power in situ. J Cataract Refract Surg 2012, in press.

Olsen T, Gimbel H. Phacoemulsification, capsulorhexis, and intraocular lens power prediction accuracy. J Cataract Refract Surg 1993; (19): 695-699.

Olsen T, Olesen H, Thim K, Corydon L. Prediction of post-operative intraocular lens chamber depth. J Cataract Refract Surg 1990a; (16): 587-590.

Olsen T, Olesen H, Thim K, Corydon L. Prediction of pseudophakic anterior chamber depth with the newer IOL calculation formulas. J Cataract Refract Surg 1992; (18): 280-285.

Olsen T, Thim K, Corydon L. Theoretical versus SRK I and SRK II calculation of intraocular lens power. J Cataract Refract Surg 1990b; (16): 217-225.

Olsen T, Thim K, Corydon L. Accuracy of the newer generation intraocular lens power calculation formulas in long and short eyes. J Cataract Refract Surg 1991; (17): 187-193.

Olsen T, Thorwest M. Calibration of axial length measurements with the Zeiss IOLMaster. J Cataract Refract Surg 2005a; (31): 1345-1350.

Olsen T, Thorwest M. Calibration of axial length measurements with the Zeiss IOLMaster. J Cataract Refract Surg 2005b; (31): 1345-1350.

Packer M, Fine I H, Hoffman R S, Coffman P G, Brown L K. Immersion A-scan compared with partial coherence interferometry: outcomes analysis. J Cataract Refract Surg 2002; (28): 239-242.

Retzlaff J. A new intraocular lens calculation formula. J Am Intraocul Implant Soc 1980; (6): 148-152.

Retzlaff J A, Sanders D R, Kraff M C. Development of the SRK/T intraocular lens implant power calculation formula. J Cataract Refract Surg 1990; (16): 333-340.

Sanders D, Retzlaff J, Kraff M, Kratz R, Gills J, Levine R, Colvard M, Weisel J, Loyd T. Comparison of the accuracy of the Binkhorst, Colenbrander, and SRK implant power prediction formulas. J Am Intraocul Implant Soc 1981; (7): 337-340.

Sanders D R, Retzlaff J, Kraff M C. Comparison of the SRK II formula and other second generation formulas. J Cataract Refract Surg 1988; (14): 136-141.

Sanders D R, Retzlaff J A, Kraff M C, Gimbel H V, Raanan M G. Comparison of the SRK/T formula and other theoretical and regression formulas. J Cataract Refract Surg 1990; (16): 341-346.

Stiles W S, Crawford B H. The luminous efficiency of rays entering the eye pupil at different points. Proc Roy Soc (London) B 1933; (112): 428-450.

Vogel A, Dick H B, Krummenauer F. Reproducibility of optical biometry using partial coherence interferometry: intraobserver and interobserver reliability. J Cataract Refract Surg 2001; (27): 1961-1968.

The invention claimed is:

1. A method for implanting a replacement intraocular lens into an eye of a patient, the method comprising the steps of:
   (a2) predicting the post-operative position of the intraocular lens in the eye of the patient by
      (i) determining the position of the existing crystalline lens in the pre-operative eye of the patient;
      (ii) determining the thickness of the crystalline lens in the pre-operative eye of the patient; and
      (iii) predicting the post-operative position of the intraocular lens relative to the position of the crystalline lens in the pre-operative eye of the patient, as a proportion of the thickness of the crystalline lens in the pre-operative eye of the patient,
      wherein the proportion is defined by a single numerical constant (C) which is determined by the intraocular lens type;
   (b2) optionally, removing the crystalline lens from the pre-operative eye of the patient;
   (c2) providing an intraocular lens; and
   (d2) implanting the intraocular lens into the eye of the patient.

2. The method according to claim 1 wherein the intraocular lens provided in step (c2) is selected using a method comprising the steps of:
   (a) predicting the post-operative position of a replacement intraocular lens in the eye of the patient using a method comprising the steps of:

(i) determining the position of the existing crystalline lens in the pre-operative eye of the patient;
(ii) determining the thickness of the crystalline lens in the pre-operative eye of the patient; and
(iii) predicting the post-operative position of the intraocular lens relative to the position of the crystalline lens in the pre-operative eye of the patient, as a proportion of the thickness of the crystalline lens in the pre-operative eye of the patient,
wherein the proportion is defined by a single numerical constant (C) which is determined by the intraocular lens type;
(b) predicting the optical properties of the post-operative eye of the patient in which an intraocular lens of known power and geometry is positioned as predicted in step (a); and
(c) selecting an intraocular lens having a power and geometry required to provide the desired optical property in the post-operative eye of the patient.

3. The method according to claim 1 wherein the intraocular lens provided in step (c2) is designed, and optionally manufactured, using a method comprising the steps of:
(a1) predicting the post-operative position of an intraocular lens in the eye of the patient using a method comprising the steps of:
(i) determining the position of the existing crystalline lens in the pre-operative eye of the patient;
(ii) determining the thickness of the crystalline lens in the pre-operative eye of the patient; and
(iii) predicting the post-operative position of the intraocular lens relative to the position of the crystalline lens in the pre-operative eye of the patient, as a proportion of the thickness of the crystalline lens in the pre-operative eye of the patient,
wherein the proportion is defined by a single numerical constant (C) which is determined by the intraocular lens type;
(b1) predicting the optical properties of the post-operative eye of the patient in which an intraocular lens of known power and geometry is positioned as predicted in step (a);
(c1) designing an intraocular lens having a power and geometry required to provide the desired optical property in the post-operative eye of the patient; and
(d1) optionally, manufacturing the intraocular lens designed in step (c1).

4. The method according to claim 1 wherein implanting the intraocular lens into the eye of the patient in step (d2) comprises implanting the intraocular lens into the capsular bag in the eye of the patient.

5. A method for treating and/or preventing and/or reducing a disease or disorder in the eye of a patient, the method comprising the steps of:
(a3) predicting the post-operative position of the intraocular lens in the eye of the patient by
(i) determining the position of the existing crystalline lens in the pre-operative eye of the patient;
(ii) determining the thickness of the crystalline lens in the pre-operative eye of the patient; and
(iii) predicting the post-operative position of the intraocular lens relative to the position of the crystalline lens in the pre-operative eye of the patient, as a proportion of the thickness of the crystalline lens in the pre-operative eye of the patient,
wherein the proportion is defined by a single numerical constant (C) which is determined by the intraocular lens type;
(b3) optionally, removing the crystalline lens from the pre-operative eye of the patient;
(c3) providing an intraocular lens; and
(d3) implanting the intraocular lens into the eye of the patient.

6. The method according to claim 5 wherein the intraocular lens provided in step (c3) is selected using a method comprising the steps of:
(a) predicting the post-operative position of a replacement intraocular lens in the eye of the patient using a method comprising the steps of:
(i) determining the position of the existing crystalline lens in the pre-operative eye of the patient;
(ii) determining the thickness of the crystalline lens in the pre-operative eye of the patient; and
(iii) predicting the post-operative position of the intraocular lens relative to the position of the crystalline lens in the pre-operative eye of the patient, as a proportion of the thickness of the crystalline lens in the pre-operative eye of the patient,
wherein the proportion is defined by a single numerical constant (C) which is determined by the intraocular lens type;
(b) predicting the optical properties of the post-operative eye of the patient in which an intraocular lens of known power and geometry is positioned as predicted in step (a); and
(c) selecting an intraocular lens having a power and geometry required to provide the desired optical property in the post-operative eye of the patient.

7. The method according to claim 5 wherein the intraocular lens provided in step (c3) is designed, and optionally manufactured, using a method comprising the steps of:
(a1) predicting the post-operative position of an intraocular lens in the eye of the patient using a method comprising the steps of:
(i) determining the position of the existing crystalline lens in the pre-operative eye of the patient;
(ii) determining the thickness of the crystalline lens in the pre-operative eye of the patient; and
(iii) predicting the post-operative position of the intraocular lens relative to the position of the crystalline lens in the pre-operative eye of the patient, as a proportion of the thickness of the crystalline lens in the pre-operative eye of the patient,
wherein the proportion is defined by a single numerical constant (C) which is determined by the intraocular lens type;
(b1) predicting the optical properties of the post-operative eye of the patient in which an intraocular lens of known power and geometry is positioned as predicted in step (a);
(c1) designing an intraocular lens having a power and geometry required to provide the desired optical property in the post-operative eye of the patient; and
(d1) optionally, manufacturing the intraocular lens designed in step (c1).

8. The method according to claim 5 wherein implanting the intraocular lens into the eye of the patient in step (d3) comprises implanting the intraocular lens into the capsular bag in the eye of the patient.

9. The method according to claim 5 wherein the disease or disorder in the eye of the patient is selected from the group consisting of: Myopia; Hyperopia; Presbyopia; Astigmatism; Refractive errors; Cataract; Opacities; and Brunescence.

10. A method for designing a replacement intraocular lens required to provide a desired optical property in the post-operative eye of a patient, the method comprising the steps of:
- (a1) predicting the post-operative position of an intraocular lens in the eye of the patient using a method comprising the steps of:
  - (i) measuring the position of the existing crystalline lens in the pre-operative eye of the patient;
  - (ii) measuring the thickness of the crystalline lens in the pre-operative eye of the patient; and
  - (iii) calculating the post-operative position of the intraocular lens relative to the position of the crystalline lens in the pre-operative eye of the patient, as a proportion of the thickness of the crystalline lens in the pre-operative eye of the patient,
  - wherein the proportion is defined by a single numerical constant (C) which is determined by the intraocular lens type;
- (b1) calculating the optical properties of the post-operative eye of the patient in which an intraocular lens of known power and geometry is positioned as predicted in step (a);
- (c1) designing an intraocular lens having a power and geometry required to provide the desired optical property in the post-operative eye of the patient; and
- (d1) manufacturing the intraocular lens designed in step (c1).

* * * * *